(12) United States Patent
Thomson et al.

(10) Patent No.: US 7,217,121 B2
(45) Date of Patent: May 15, 2007

(54) METHOD AND APPARATUS FOR IMPROVED PROCESS CONTROL IN COMBUSTION APPLICATIONS

(76) Inventors: Murray J. Thomson, 3 Easson Avenue, Toronto, Ontario (CA) M6S 3W6; Jason J. Nikkari, 3806 Milkwood Crescent, Mississauga, Ontario (CA) L5N 8H4; Gervase I. Mackay, 32 Feagan Dr., West Hill, Ontario (CA) M1C 2B7; Alak Chanda, 2 Hemlark Court, Brampton, Ontario (CA) L6S 2B7

( * ) Notice: Subject to any disclaimer, the term of this patent is extended or adjusted under 35 U.S.C. 154(b) by 0 days.

(21) Appl. No.: 10/819,227

(22) Filed: Apr. 7, 2004

(65) Prior Publication Data

US 2004/0191712 A1    Sep. 30, 2004

Related U.S. Application Data

(63) Continuation of application No. 09/888,616, filed on Jun. 26, 2001, now abandoned.

(60) Provisional application No. 60/245,567, filed on Nov. 6, 2000, provisional application No. 60/214,008, filed on Jun. 26, 2000.

(51) Int. Cl.
*G01N 21/62* (2006.01)

(52) U.S. Cl. .............. 431/12; 431/2; 431/75; 431/76; 75/375; 266/99; 250/339.01; 250/339.1; 356/438

(58) Field of Classification Search ............ 431/2, 431/12, 18, 75, 76; 340/575; 356/438, 439; 250/339.01–339.08, 338.5, 339.1; 75/375; 266/99

See application file for complete search history.

(56) References Cited

U.S. PATENT DOCUMENTS

2,874,763 A * 2/1959 Hobbs ..................... 431/79

(Continued)

FOREIGN PATENT DOCUMENTS

EP    0084726    * 12/1982

(Continued)

OTHER PUBLICATIONS

Twenty-Seventh Symposium (International) On Combustion, vol. 1, THE Combustion Institute, Pittsburgh, Pennsylvania; pp. 103-111, Furlong et al, 1998.*

(Continued)

*Primary Examiner*—Carl D. Price
(74) *Attorney, Agent, or Firm*—Bereskin & Parr

(57) ABSTRACT

This invention relates to a method and apparatus for improved process control in combustion applications, and particularly those relating to the steelmaking industry. An apparatus is provided for process control in a combustion application comprising a laser to transmit a near-infrared laser beam through off-gas produced by the combustion application, a detector to detect the transmitted laser beam and convert the detected laser beam to an electrical signal, and a control system for providing adjustment of select inputs to the combustion application in response to the electrical signal from the detector. The method of this invention comprises transmitting a near-infrared laser beam through off-gas produced by the combustion application, detecting the transmitted laser beam, and adjusting select inputs of the combustion application in response to the detected transmitted laser beam.

24 Claims, 20 Drawing Sheets

U.S. PATENT DOCUMENTS

| | | | |
|---|---|---|---|
| 3,564,237 A * | 2/1971 | Takeuchi et al. | 250/304 |
| 3,790,797 A * | 2/1974 | Sternberg et al. | 250/345 |
| 3,860,818 A * | 1/1975 | Stalder et al. | 250/343 |
| 4,043,742 A * | 8/1977 | Egan et al. | 431/12 |
| 4,288,062 A * | 9/1981 | Gupta et al. | 266/88 |
| 4,549,080 A * | 10/1985 | Baskins et al. | 250/343 |
| 4,560,873 A * | 12/1985 | McGowan et al. | 250/339.09 |
| 4,616,137 A * | 10/1986 | Goff et al. | 250/554 |
| 4,653,998 A * | 3/1987 | Sohma et al. | 431/79 |
| 4,829,183 A * | 5/1989 | McClatchie et al. | 250/346 |
| 4,896,965 A * | 1/1990 | Goff et al. | 356/417 |
| 4,953,390 A * | 9/1990 | Krempl et al. | 73/116 |
| 5,017,004 A * | 5/1991 | Cross et al. | 356/336 |
| 5,029,117 A * | 7/1991 | Patton | 702/135 |
| 5,252,060 A * | 10/1993 | McKinnon et al. | 431/12 |
| 5,313,044 A * | 5/1994 | Massoud et al. | 219/121.85 |
| 5,332,901 A * | 7/1994 | Eckles et al. | 250/345 |
| 5,488,476 A * | 1/1996 | Mansfield et al. | 356/512 |
| 5,506,685 A * | 4/1996 | Grasdepot | 356/409 |
| 5,599,179 A * | 2/1997 | Lindner et al. | 431/12 |
| 5,621,166 A * | 4/1997 | Butler | 73/116 |
| 5,886,247 A * | 3/1999 | Rabbett | 73/23.2 |
| 5,984,998 A * | 11/1999 | Ottesen et al. | 75/375 |
| 6,045,353 A * | 4/2000 | VonDrasek et al. | 431/79 |
| 6,071,114 A * | 6/2000 | Cusack et al. | 431/79 |
| 6,122,042 A * | 9/2000 | Wunderman et al. | 356/73 |
| 6,181,411 B1 * | 1/2001 | Harris et al. | 356/4.01 |
| 6,227,842 B1 * | 5/2001 | Lemelson et al. | 431/12 |
| 6,370,486 B1 * | 4/2002 | Sivathanu | 702/135 |
| 6,422,056 B1 * | 7/2002 | Miyai et al. | 73/1.06 |
| 6,455,851 B1 * | 9/2002 | Lord et al. | 250/338.5 |
| 6,468,069 B2 * | 10/2002 | Lemelson et al. | 431/12 |
| 6,573,991 B1 * | 6/2003 | Debreczeny et al. | 356/336 |
| 2002/0031737 A1 * | 3/2002 | Von Drasek et al. | 431/79 |

FOREIGN PATENT DOCUMENTS

| | | | |
|---|---|---|---|
| EP | 0766080 | * | 2/1997 |
| EP | 000922908 | * | 6/1999 |
| EP | 000922908 A1 | * | 6/1999 |
| EP | 000967440 A2 | * | 12/1999 |

OTHER PUBLICATIONS

AIAA 96-2226 Diode Laser Sensors for Combustion and Aeroengine Emissions Testing: Applications to CO, CO2, OH, and NO; Sonnenfroh et al; 19th AIAA Advanced Measurement and Ground Testing Technology Conference; Jul. 17-20, 1996; New Orleans, LA; pp. 1-10.*

Frequency-modulation spectroscopy for trace species detection: theory and comparison among experimental methods; Joel Silver; Feb. 20, 1992; vol. 31 No. 6/ Applied Optics; pp. 707-717.*

Measuremens of CO, CO2, OH, and H2O in room temperature and combustion gases by use of a broadly current-tuned multisection InGaAsp diode laser; Upschulte et al; Applied Optics/ vol. 38 No. 9/ Mar. 20, 1999; pp. 1506-1512.*

* cited by examiner

METHOD AND APPARATUS FOR IMPROVED PROCESS CONTROL IN COMBUSTION APPLICATIONS

This application is a continuation of application Ser. No. 09/888,616, filed Jun. 26, 2001 now abandoned, the entirety of which is hereby incorporated by reference, which claims the benefit of U.S. Provisional Application No. 60/245,567, filed Nov. 6, 2000, the entirety of which is hereby incorporated by reference, and also which claims the benefit of U.S. Provisional Application No. 60/214,008, filed Jun. 26, 2000, the entirety of which is hereby incorporated by reference.

FIELD OF THE INVENTION

This invention relates to a method and apparatus for improved process control in combustion applications, and particularly those relating to the steelmaking industry.

BACKGROUND OF THE INVENTION

Modern steelmaking industries need to monitor the process characteristics of the steelmaking process due, in part, to the unknown composition of scrap steel that can give rise to inaccuracies in achieving the desired end point concentration of carbon and melt temperature in the final steel product. Further, real time process monitoring in the steelmaking process is required to ensure safety, minimize pollutant emissions, and maximize productivity and energy efficiency—factors the steelmaking industry is sensitive to, due to increasing environmental regulations and ever greater competition within the industry.

Steelmaking technologies of today generally use either basic oxygen furnaces (BOFs) or electric arc furnaces (EAFs). EAFs are enjoying an increase in market share due, in part, to the EAFs ability to use 100% recycled scrap metal which, in turn, results in lower energy requirements per unit production (a large part of the energy savings for EAFs arises from avoidance of mining, smelting, and refining the raw ore). Additional savings can occur since the primary energy source for EAFs is electrical energy, rather than fossil fuels—particularly desirable given that the steelmaking industry is a source of both greenhouse gases (mainly $CO_2$), as well as pollutants such as CO, $NO_x$ and other noxious substances, such as dioxins, hydrocarbons, and other particulates.

Notwithstanding the above benefits of EAFs current EAFs are often limited to energy efficiencies on the order of about 50–60%. Further efficiency to the steelmaking process can be achieved by improved process control during the combustion application, particularly by using non-intrusive, real time measurements of selected off-gases and temperature produced during the combustion application. For example, reducing CO to 1–2% from current industry levels in the 10–30% range can result in substantial energy savings for large EAF operations. CO provides a good empirical measure of chemical energy losses while exhaust gas temperature allows a reasonable estimate of thermal energy losses.

It can be appreciated that the requirements for a sensor to measure off-gas exhaust from an EAF is primarily driven by considerations of the harsh environment that exists in the exhaust duct where the off-gas sensor is located. Exhaust temperatures can range from about 1000 K to about 2000 K. Moreover, duct gases can have high dust concentrations that can interfere with the operation of the sensor. Further, chunks of molten slag can occasionally spew up into the duct and interfere with or damage the sensors.

Many commercial steel mills use extractive techniques to obtain a sample of off-gas from the exhaust. The extracted gas is cooled then analyzed using commercially available mass spectrometry or non-dispersive infrared absorption methods or chemical cells. It can be appreciated, however, that the steps required to obtain a sample of the off-gas from extractive techniques can result in time delays in acquiring the data. By contrast, a process control that uses real time sensors can obtain selective measurements of the off-gas constituents and provide adjustment of the inputs to a furnace (such as oxygen, fuel, electric current, etc.) on a continuous feedback loop.

Due to the harsh environment, temperature measurements are generally not available in the EAF exhaust duct because thermocouples are unable to withstand the demanding conditions.

Optical techniques, for example, can provide a non-intrusive sensor for measuring real time composition of the off-gas and temperature in an exhaust duct. The non-intrusive nature provides numerous operation and maintenance advantages in the harsh exhaust duct environment. Moreover, optical techniques offer the benefit of providing a line average concentration and temperature measurement, rather than a point measurement, which can provide more accurate and reliable approximation of average conditions with an exhaust duct of a furnace. Optical techniques generally utilize a laser beam passing straight across an exhaust duct.

One example of an optical based method and apparatus for off-gas composition sensing is disclosed in the U.S. Pat. No. 5,984,998. This patent discloses transmitting a tunable diode laser with wavelengths in the mid-infrared (mid-IR) region through the off-gas produced by a steelmaking furnace, and measuring the transmitted laser beam to produce a signal based on the wavelength absorption properties of the different off-gases. This measurement provides measurements of the gaseous constituents of the off-gas. Mid-IR diode lasers provide good sensitivity for certain molecules of interest in the off-gas, particularly, $CO_2$, CO, and $H_2O$.

Mid-IR laser systems, however, have certain practical limitations, particularly when operating beyond the 3.0 μm wavelengths into the mid-IR range. For example, a Pb-salt diode laser operates significantly below room temperature, necessitating cryogenic cooling. This adds to the complexity and cost of a steelmaking process control system.

Other problems using a mid-IR based laser diode sensor include signal saturation during high emission portions of the steelmaking process. Signal saturation can result in loss of process information during times of high emissions. Further, mid-IR light does not propagate readily through available fibre optics. Accordingly, the sensor should be located near the harsh environment of the exhaust duct of the furnace. This can result in a need to design special protective equipment such as water-cooling jackets and airtight seals.

In addition, mid-IR systems use mirrors to project and align the laser beam from the instrument through the desired measurement location in the exhaust duct. Ambient dust can be a problem on the electrical motors necessary to control the mirrors.

SUMMARY OF THE INVENTION

One of the most promising ways to meet competitive and regulatory pressure is through significant process control improvements. The attributes of tunable diode lasers operating in the near-infrared match very well with many of the requirements for improved process control in numerous combustion applications, including electric arc furnaces (EAFs).

The present invention provides a system for process control in a combustion application, comprising a tunable diode laser for generating a frequency modulated near-infrared laser beam, a transmitting means for transmitting the near-infrared laser beam through off-gas produced by the combustion application, a detecting means for detecting the transmitted laser beam, a controller means for analyzing the detected laser beam for select CO and H2O absorption lines to determine CO concentration, and for producing an electrical signal in response to CO concentration, and a control system for providing adjustment of select inputs to the combustion application in response to the electrical signal from the controller means.

In the invention disclosed, the controller comprises means for providing predetermined calibration curves to determine CO concentration. In particular, the calibration curve is CO concentration as a function of CO absorption lines and temperature. For the embodiment disclosed, the controller determines the temperature of the off-gas from analysis of the H2O absorption lines, and particularly H2O absorption lines that respond differentially to changes in temperature. In the preferred embodiment disclosed the temperature of the off-gas is determined from the ratio of two H2O absorption lines. The CO absorption lines are chosen where they have a profile of strong lines as compared to H2O.

For the purpose of this invention the wavelength of a near-infrared laser beam is in the range of about 0.7 µm to about 3.0 µm. In one embodiment the transmitting means is a tunable diode laser operating with a wavelength in the range of about 1.5 µm to about 1.7 µm. In a further embodiment of the invention the transmitting means is a distributed feedback laser operating with a wavelength in the range of about 1.57 µm to about 1.59 µm.

In a preferred embodiment of the invention the select inputs to the combustion application comprise, for example, either singly, or in combination, oxygen, fuel, and electric power—particularly where this invention is practiced on an electric arc furnace as a combustion application.

This invention also provides for a method of process control in a combustion application, comprising:

a) transmitting a frequency modulated near-infrared laser beam through off-gas produced by the combustion application to target CO and H2O;

b) detecting the transmitted laser beam; and c) analyzing the detected laser beam for select CO and H2O absorption lines;

d) determining CO concentration from the CO and H2O absorption lines;

e) adjusting select inputs of the combustion application in response to the CO concentration.

In the method disclosed the CO concentration is determined using predetermined calibration curves. In particular, the calibration curve is CO concentration as a function of CO absorption lines and temperature. For the embodiment disclosed, the method targets H2O absorption lines to determine the temperature of the off-gas, and particularly H2O absorption lines that respond differentially to changes in temperature. In the preferred embodiment disclosed the temperature of the off-gas is determined from the ratio of two H2O absorption lines. Moreover, the method of a preferred embodiment of this invention targets CO as one off-gas for analysis, and particularly where CO has a profile of strong lines compared to H2O. While temperature measurements are necessary from a spectroscopic point of view, they are also valuable from other perspectives, including process control, quantification of exhaust gas thermal energy, improved air pollution control system design and operation, and others.

BRIEF DESCRIPTION OF THE DRAWINGS

For a better understanding of the present invention and to show more clearly how it would be carried into effect, reference will now be made, by way of example, to the accompanying drawings that show a preferred embodiment of the present invention, and in which.

DESCRIPTION OF THE PREFERRED EMBODIMENT

Two dominant furnace technologies used in contemporary steelmaking are basic oxygen furnaces (BOFs) and electric arc furnaces (EAFs). As mentioned in the background of the invention, EAFs are enjoying an increase in market share due, in part, to the ability of EAFs to process 100% recycled scrap steel and its primary reliance on electrical energy, rather than fossil fuels, as an energy source for the combustion application. Accordingly, this invention shall be described referencing EAFs, but it is to be understood that the methods and apparatus disclosed are not to be limited to EAFs, but rather, can apply to any combustion application requiring real-time monitoring of off-gas composition and temperature, and particularly for process control.

Figure 1:
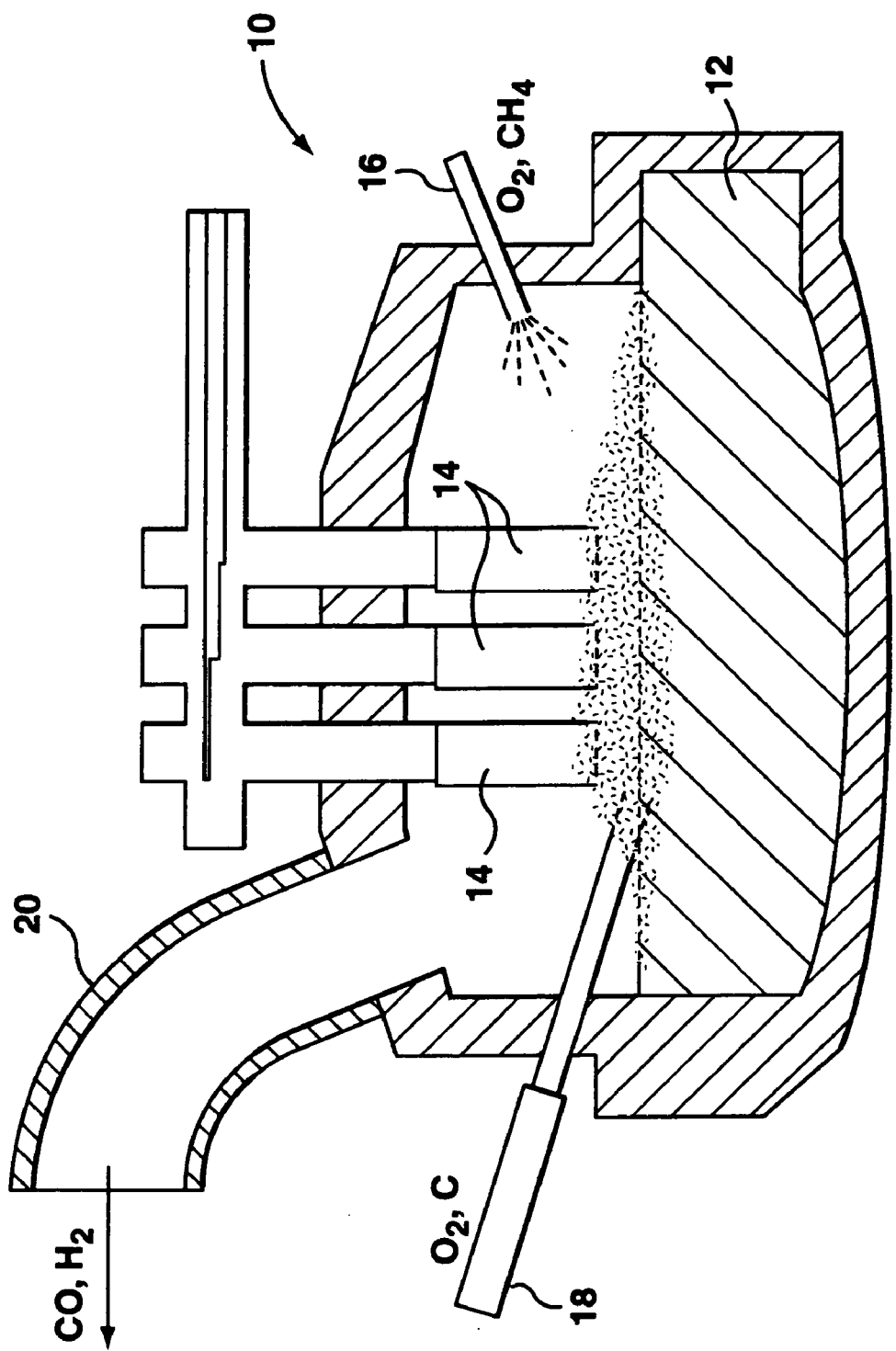
FIG. 1 is a schematic view of a typical electric arc furnace.

An EAF 10 is shown in FIG. 1. In general an EAF is first charged (ie., raw material is added to the furnace) with a mixture of metal (typically scrap metal) and lime. The metal is then melted (shown at 12) by creating electric arcs from the electrodes 14. The temperature around the arcs can rise to 12,000° C. At this temperature a 100 tonne charge takes about 60 minutes to melt. After melting, carbon and oxygen gas are both blown or injected into the furnace at 16 and 18 to form a foamy slag layer generating and releasing large quantities of CO. The oxygen also oxidises elements in the metal, such as carbon, silicon and manganese. The acidic oxides combine with the basic lime to form a neutral slag that can be poured off the surface. Carbon monoxide is also formed and escapes as a gas through exhaust duct 20. The metal is then allowed to run out of the furnace (known as tapping) into a ladle for secondary processing and casting, as needed.

Figure 2:
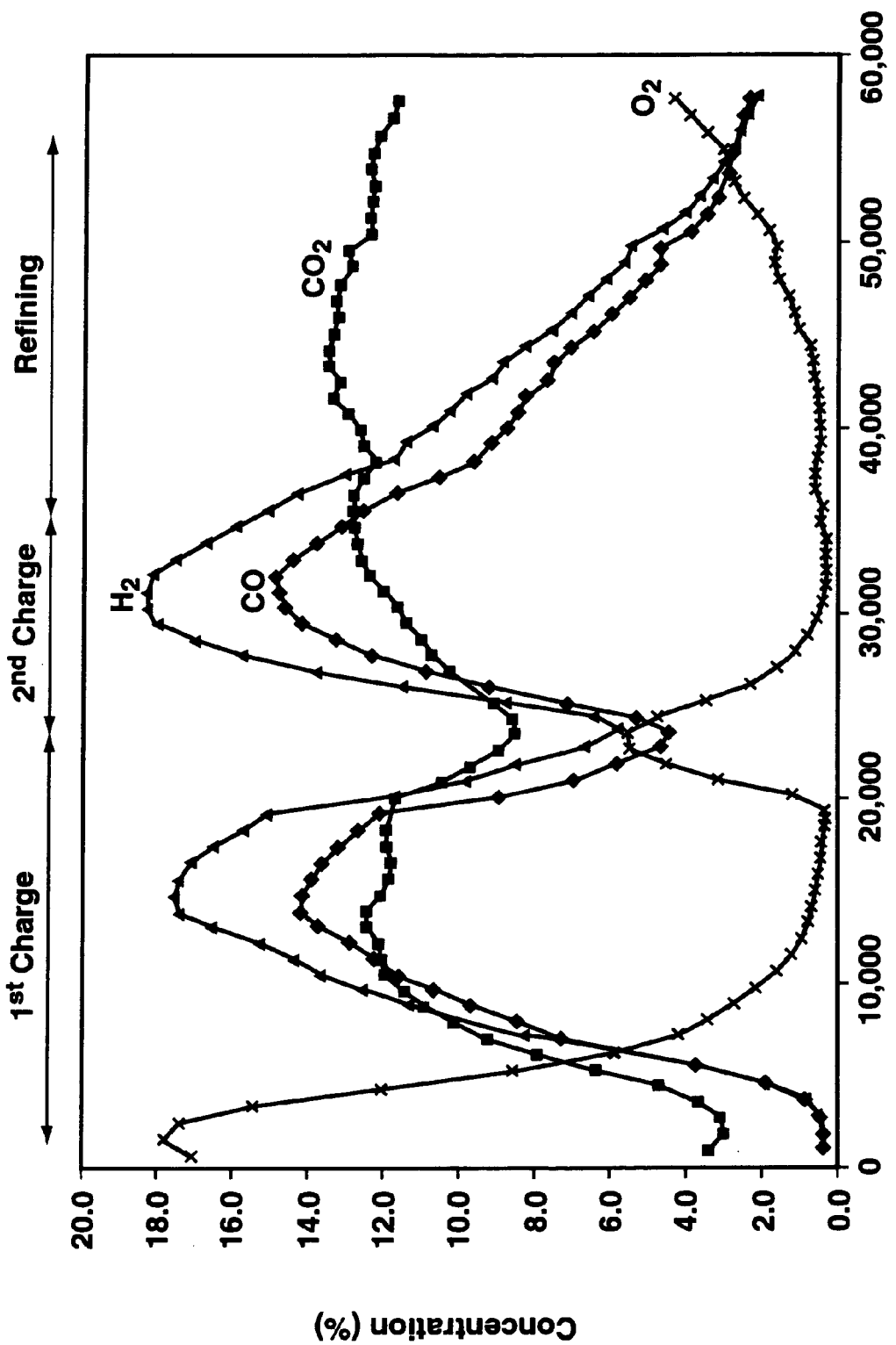
FIG. 2 is a graph of emissions of major off-gasses from an electric arc furnace during a typical tap-to-tap cycle.

Significant gases emitted from steelmaking furnaces such as EAFs include CO, $CO_2$, $NO_x$, $H_2O$, $O_2$, $H_2$, and other gases, such as hydrocarbons. The percent concentration of gas emissions from a typical EAF are shown in FIG. 2, which plots extractively measured off-gas composition averaged over approximately 100 runs at a full scale EAF. It can also be appreciated from FIG. 2 how rapidly the conditions within an EAF can change. Variations are caused by many factors, such as, for example, charging of the EAF with scrap metal, combustion of oil and other combustible impurities, as well as injections of $O_2$ (blown into the furnace), $CH_4$, and carbon. Further, the quality of scrap steel can vary from one batch to the next.

CO gives a good representation of chemical energy that is wasted when oxygen gas is blown into the furnace. $H_2$ emissions also provide a good representation of chemical energy not utilized effectively in the process. FIG. 2 shows that CO and $H_2$ track each other very closely (the oxygen blown into the furnace reduces both compounds concurrently releasing the chemical energy of each compound). Accordingly, so long as one of either CO or $H_2$ is measured, the required information from a process control perspective is obtained.

It is also desirable to monitor temperature of the off-gas and hence obtain a measure of thermal energy losses in the combustion application. As will hereinafter be detailed, this invention provides for a method of targeting $H_2O$ to measure temperature of the off-gas.

The absorption and emission of light is related to a change in the molecular energy from one level to another, or the energy transition. In absorption, electrons are elevated to a higher energy state (describing a change in rotational energy, vibrational energy, electronic energy and/or any combinations of those), and during emission this energy is discharged. The width of a typical absorption peak is less than 0.01 nm. Diode laser based optical absorption is based, in part, on conventional absorption spectroscopy, and, in particular, follows Beer's Law:

$$\frac{I}{I_0} = \exp[-S(T) \cdot \phi(T, P) \cdot n_i \cdot L] = \exp(-A) \quad (1)$$

Where I is the laser intensity reaching the detector, $I_0$ is the incident laser intensity, S(T) is the temperature dependent line strength, $\Phi(T,P)$ is the temperature and pressure dependent line shape function, and takes into account both temperature (Doppler) and pressure (collision) broadening mechanisms, n is the number density of the absorbing species, L is the absorption path length, and A is the absorbance.

Optical systems that offer real time analysis of the off-gas are generally based on tunable diode lasers (TDLs). In particular, with a diode laser based system response times can be less than a second.

Near-infrared (near-IR) TDLs (for purposes of this invention a near-IR laser operates with wavelengths in the range of about 0.7 μm to about 3.0 μm) offer certain advantages for use in an optical sampling system. For example, near-IR TDLs can operate over a temperature range of about 0° C. to about 50° C. This near room temperature operation allows lasing to be achieved using, for example, thermoelectric heating and cooling without undue complexity or energy requirements. Moreover, the wavelengths of near-IR TDLs typically match the optical loss minima in quartz fibres, facilitating the use of fibre optic cables. Moreover, decreased sensitivity of near-IR TDLs has a benefit in that non-linear absorption can be reduced (allowing Beer's Law to remain applicable for the measurement). It should be noted that decreased sensitivity of near-IR TDLs is generally not an issue in measuring the combustion of select off-gasses, such as CO, which generally need to be measured in percentages, rather than at trace levels.

For quantitative measurements with the best sensitivity, a laser should operate in a single mode so that only one wavelength is emitted. Near-IR TDLs have a multimode output near the lasing threshold. With increasing current applied to the laser, the output evolves to a single mode output. Near-IR lasers employing distributed feedback (DFB) are constrained to single mode operation under all conditions. DFB lasers are fabricated with a miniature grate, aligned along the length of the gain region.

Single mode near-IR TDLs are suited for the detection of gases by optical absorption, or spectroscopy. The laser wavelengths coincide with the absorption lines of the targeted gas molecules. Moreover, the laser wavelengths typically are less than about 50 MHz, meaning that, in general, the wavelengths are typically narrower than the pressure and temperature broadened line widths of targeted molecules. This high spectral resolution allows line specific measurements of targeted species. The targeted species for industrially or environmentally significant gases from EAFs that may be measured by near-IR TDL spectroscopy include, for example, oxygen, water vapour, methane, acetylene, carbon monoxide, carbon dioxide, hydrogen halides, ammonia, hydrogen sulfide, and nitrogen oxides.

Near-IR TDLs are easily tunable with current and temperature, and for current designs having wavelengths below about 2.4 μm they operate at room temperature, dissipating about 100 mW of power. Moreover, DFB near-IR TDLs show continuous single mode tuning at the rate of about 0.5 $cm^{-1}$/° C. An additional benefit of operating in the near-IR is that pressure broadening does not present as large a problem as it does at the longer wavelengths. This is a benefit for measurements conducted at or above atmospheric pressure, as in the exhaust duct of an EAF.

One characteristic that limits measurement sensitivity is intensity noise or fluctuations associated with output power. The fundamental quantum limit, in the absence of any attempt to produce "squeezed light," is the shot noise associated with the detected laser power. Relative shot noise (RSN) is inversely proportional to the detected power. In addition to RSN, DFB lasers produce what is referred to as relative intensity noise (RIN). RIN is expressed as the fluctuations in the detected power per unit bandwidth, divided by the detected power squared. RIN arises from amplified spontaneous emission and is inversely proportional to the cube of the detected power. At sufficiently high levels of detected power, RIN will be less than the RSN, and the limit to the laser output beam will be approximately the shot noise. Typically, the intensity noise of DFB lasers is about 5 dB $Hz^{-1/2}$ above the shot noise limit. This suggests that near-IR TDLs have best S/N ratio at high operating powers, limited only by facet damage.

Near-IR instruments probe overtones or combinations of the fundamental vibrational transitions. To achieve the required sensitivity a TDL can employ frequency modulation detection techniques. This can allow a TDL to measure absorbencies as small as 1 part in about $10^5$. Frequency modulation is sometimes referred to as "wavelength modulation," "derivative spectroscopy," or "harmonic detection." In practice, however, frequency modulation spectroscopy and wavelength modulation spectroscopy differ only with regard to the choice of modulation frequency: frequency modulation spectroscopy involves modulation frequencies greater than the absorption line width; wavelength modulation spectroscopy involves modulation frequencies smaller than the absorption line width. Accordingly, frequency modulation spectroscopy produces distinct laser sidebands whereas wavelength modulation spectroscopy generates a continuous distribution of laser wavelengths. Where absorption line widths exceed 1 GHz this distinction becomes important. This can occur, for example, when working with gases at atmospheric pressure or higher. Moreover, elevated temperatures increase the line widths even further due to Doppler broadening. These are the type of conditions that typically exist in the exhaust duct of an EAF.

For these reasons, a preferred embodiment of this invention uses frequency modulation spectroscopy, and particularly operated at MHz frequencies: matching the modulation to the absorption line width only requires a change of the modulation amplitude. Moreover, by modulating the laser frequency at MHz rates, the measurement bandwidth is shifted to higher frequencies where the laser excess noise is substantially reduced to the shot noise limit. The laser wavelength can be modulated sinusoidally by an amount comparable to the wavelength of the target optical absorption line. This modulation is readily effected by adding a small AC component to the laser current. Phase sensitive electronics measure the detector photocurrent at the modulation frequency, f, or a harmonic nf. In the limit where the modulation amplitude is small compared with the spectral feature line width, the resulting demodulated signal is the nth derivative with respect to wavelength of the direct transmission spectrum. Absolute absorbencies are obtained by dividing the demodulated AC signal by the detector DC output.

It is to be understood, however, that alternate sensitive techniques are possible to those skilled in the art. For example, one alternative technique is based on signal detection using a balanced ratiometric detector. This technique is known to yield optical absorbencies as low as 1 ppm. With this technique, cancellation of excess laser amplitude noise is achieved by electronically balancing (rather than optically balancing) the photocurrents from each photodiode detector.

EXAMPLE

From the above analysis the preferred embodiment will be described using a near-IR DFB TDL as a process sensor for use with EAFs. For a better understanding of the present invention and to show more clearly how it would be carried into effect, the following illustrative example is provided. The example is in the form of an experiment and methodology used to select the near-IR TDL laser. Available modelling tools and research was used to assist in the selection of a promising laser diode material for the wavelengths of interest to combustion applications. For example, the U.S. Air Force provides atmospheric modelling programs (known as HITRAN and HITEMP) that can be used to select an optimum wavelength region of the species of interest for combustion applications, such as CO and $H_2O$. In particular, HITEMP modelling is available for CO, $CO_2$, and $H_2O$, whereas HITRAN modelling has a much wider selection but for complex molecules is only accurate at low temperatures. Unfortunately, current spectral databases are not well verified at the high temperatures present in combustion applications such as EAFs. Research conducted to date indicates that while models such as HITEMP appear to predict line position and strength relatively well for divalent compounds such as, for example, CO, there are significant inaccuracies for triatomic compounds such as, for example, $CO_2$ and $H_2O$. It has been suggested that HITEMP is a reasonably good predictor of the high temperature absorption of water vapour: while individual line positions and strengths are often erroneous, global positioning of the strongest water features is largely correct. When working in spectrally dense regions, however, even small errors in predicted position and strength can be critical.

Research and independent experimental confirmation by the present inventors indicate that HITEMP predictions for $CO_2$ line strengths in the near-IR are very poor and appear to over predict $CO_2$ line strengths. The difficulty in modelling triatomic absorption lines is thought to be due to the increased number of possible energy states available to these compounds, particularly at high temperatures. Notwithstanding the limitations of high temperature modelling tools, there is little alternative but to use them when selecting a laser to investigate spectral ranges.

In deciding upon the near-IR laser diode to be used in this experiment, several factors were taken into consideration, including:

Strong spectroscopic line(s) for the species of interest, namely, CO, and $H_2O$, over the full range of temperature conditions ($\cong$1000–2000 K);

Minimal interference with other species and particularly $H_2O$; and

Availability/cost of the laser diode and other system components.

Once the laser is selected, the spectroscopy in the target wavelength regions are established for the range of environmental conditions to be tested. Due to the uncertainty in high temperature modelling results, particularly for $H_2O$, it is necessary conduct laboratory tests in order to confirm, and in some cases establish, the spectroscopy over the wavelength range and environmental conditions of interest. Once the spectroscopy is established over a representative range of test conditions, the optimal CO and $H_2O$ absorption peaks can be selected. Accurate calibration curves over the full range of test conditions are then established using the laboratory set-up shown in FIG. 3.

Figure 3:
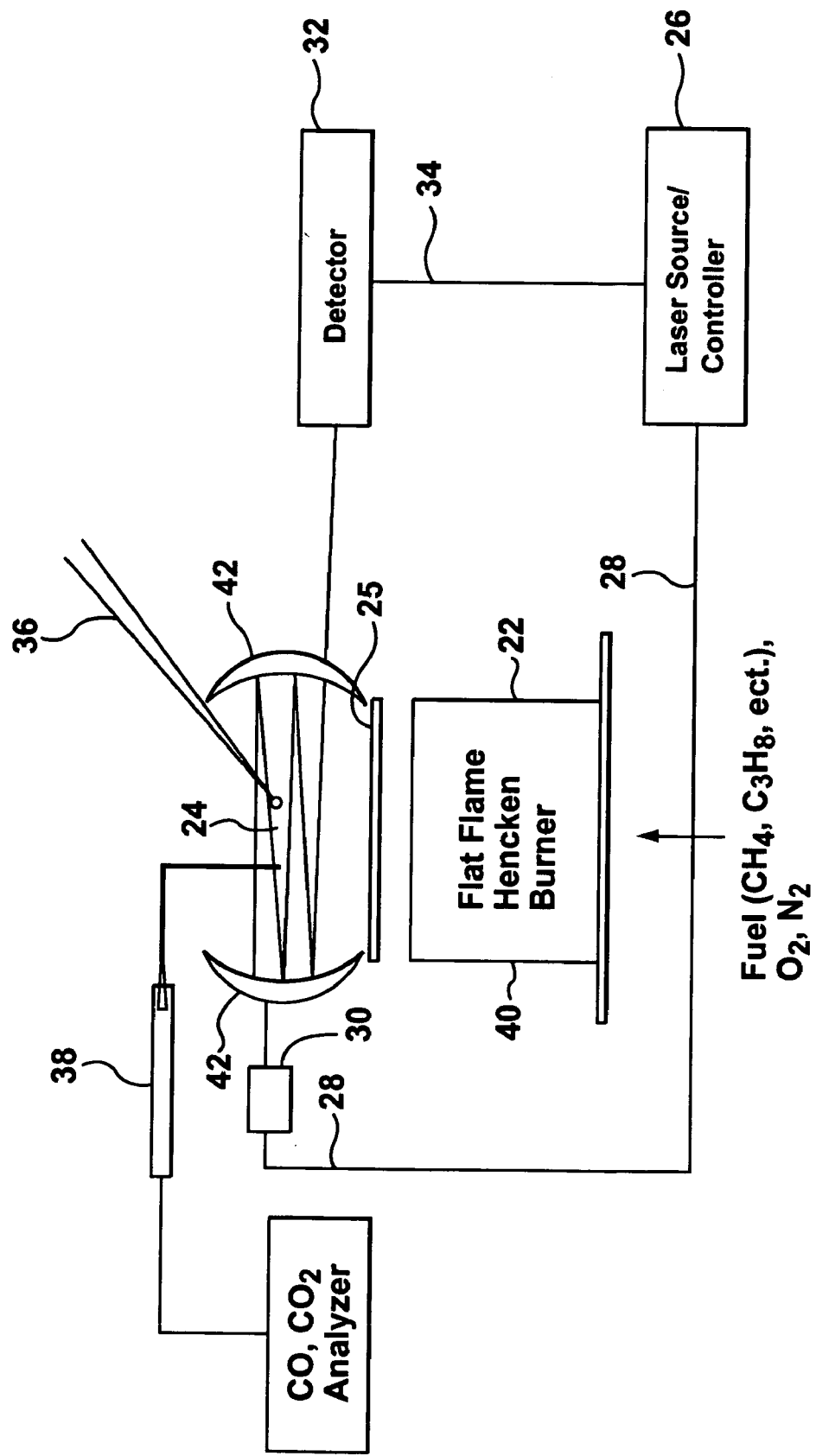
FIG. 3 is a schematic view of an experimental set-up.

In the experimental set-up of FIG. 3 a source of high temperature and combustion gases 22 is provided to simulate a combustible environment of an EAF and particularly the exhaust duct as at 24. A laser beam is transmitted from source 26 through fibre optic cable 28 to launch assembly 30. The laser beam is then transmitted from launch assembly 30 across region 24 to detector 32, which feeds the electronic signal back to source 26 through a coaxial cable 34. In addition, the experimental set-up features in region 24 a thin-wire thermocouple 36 to detect the temperature and an extractive analyzer 38 to measure the CO and $CO_2$.

To study the laser response to a wide range of high temperature target gas concentrations, a flat flame Hencken diffusion burner 40 was selected as the source of high temperature and combustion gases 22. In order to increase the measurement sensitivity, and to more accurately represent typical path lengths present in region 24 as in full scale EAFs, a multi-pass optical absorption cell 42 was created for the lab testing. An open path Herriot type multi-pass optical set-up was used. Thermocouple 36 is a 0.020" diameter, unsheathed, type "R" (Pt-Rh) thermocouple from Omega Engineering Inc. This type of thermocouple is able to withstand temperatures up to about 1723 K, and has a fast response time.

Figure 4:
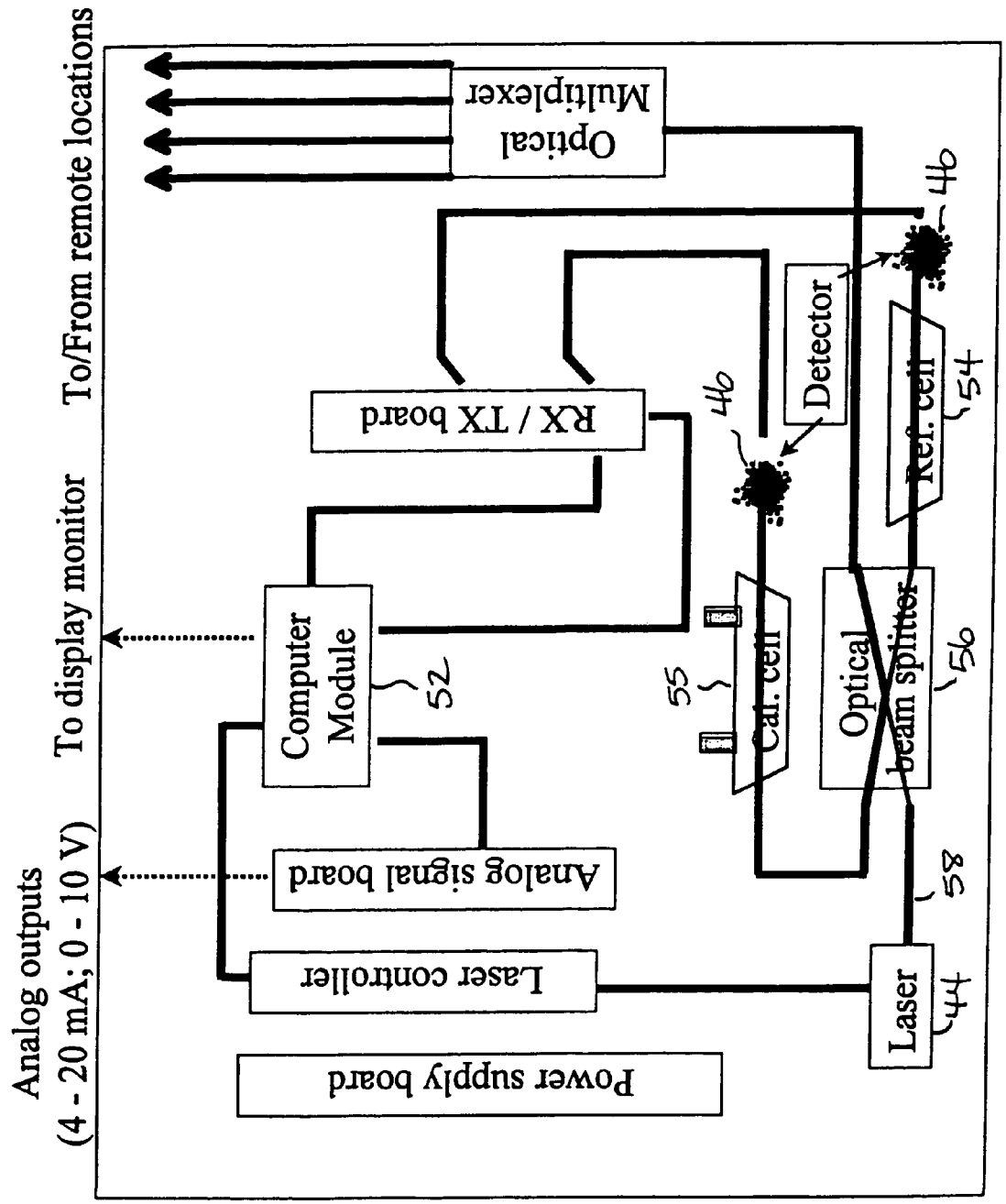
FIG. 4 is a schematic view of a laser used in the experimental set-up of FIG. 3.

The laser source 26 used in this study is from Unisearch Associates Inc. (model number LCM-03) and is illustrated in FIG. 4. This laser utilizes two-tone frequency modulation to increase the detection sensitivity. The source 26 contains the DFB diode laser 44 and its temperature and current circuits, the detector 46 and its circuitry, the connector 48 to the fibre optic cable to launch assembly 30, the connector 50 for coaxial cable 34 from detector 32, the interface to the computer 52 for automatic control and data acquisition and logging, and a reference cell 54 containing measurements of known concentrations of CO and $CO_2$.

Using a 90/10 beam splitter 56, approximately 10% of the laser beam 58 is passed to reference cell 54 to lock the laser onto the selected absorption feature. For room temperature measurements (approximately 0–50° C.) reference cell 54 at atmospheric pressure (approximately, 100 kPa) can also serve as a secondary calibration standard. For high temperature applications, however, as, for example, found in the exhaust duct of an EAF, the calibrations found in reference cell 54 for the targeted species are inadequate. High temperature applications require calibration curves to be calculated and stored, for example, in computer 52, or, for example, in a calibration cell 55. The remaining 90% of the beam is used for the measurement channel.

In particular, the laser beam is brought to one or more of the measurement locations as far as several kilometres away using a standard silica fibre optic cable 28, such as those used in the telecommunication industry. This allows the controller to be placed in any suitable location within an industrial site far away from hazardous or explosive conditions in an EAF to which the launch and detector assemblies may be exposed. To decrease connection losses and back-reflections, FC/APC fittings, such as part number F1-2069APC as supplied by Fiber Instrument Sales Inc. of New York, are used. The controller is operated by an on-board computer. The data is also directly linked to a separate computer for data processing and storage via an RS-232 port provided with the controller unit.

Figure 5:
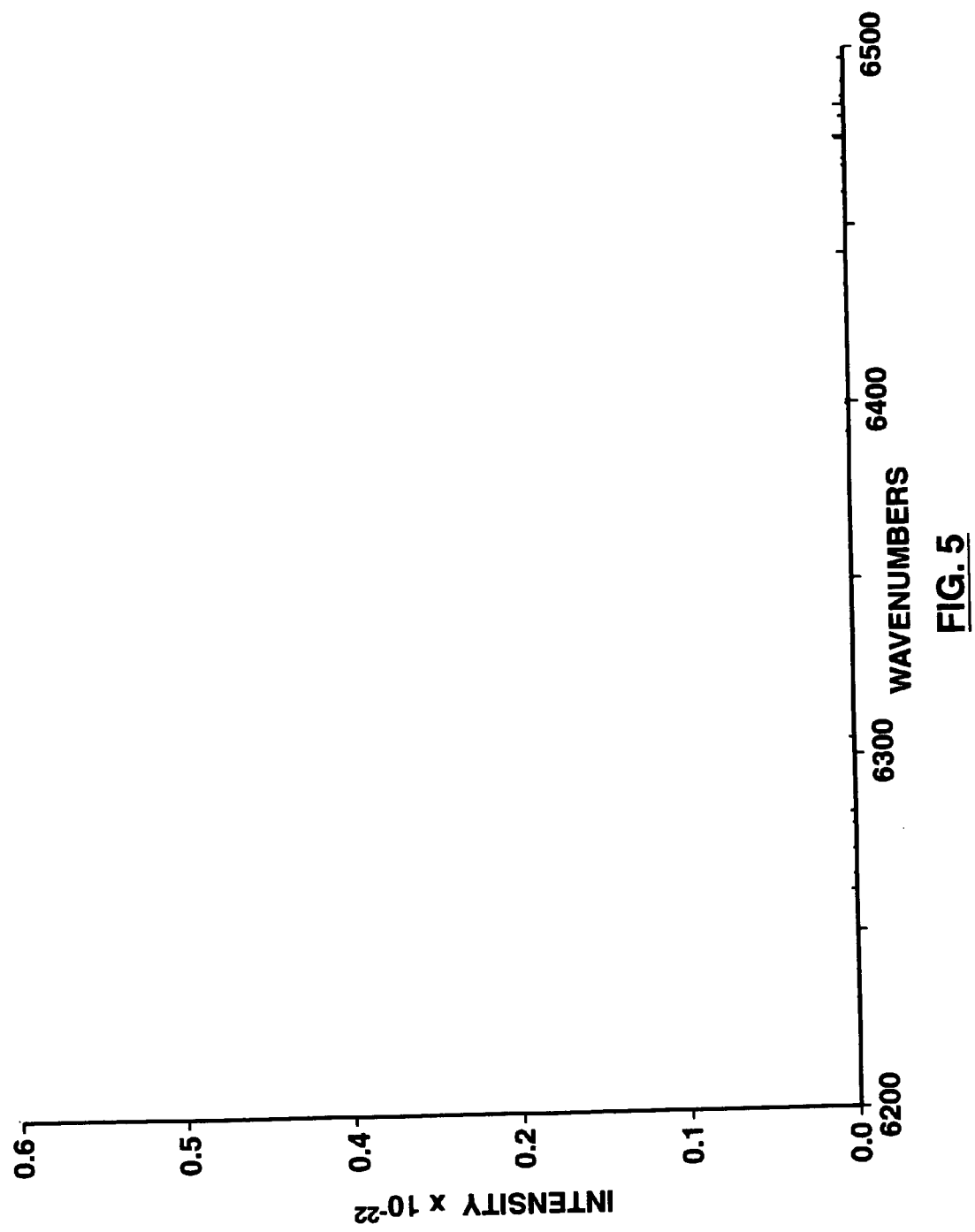
FIG. 5 is a graph of the U.S. Air Force's HITRAN modelling results for $H_2O$ at 300 K.
Figure 6:
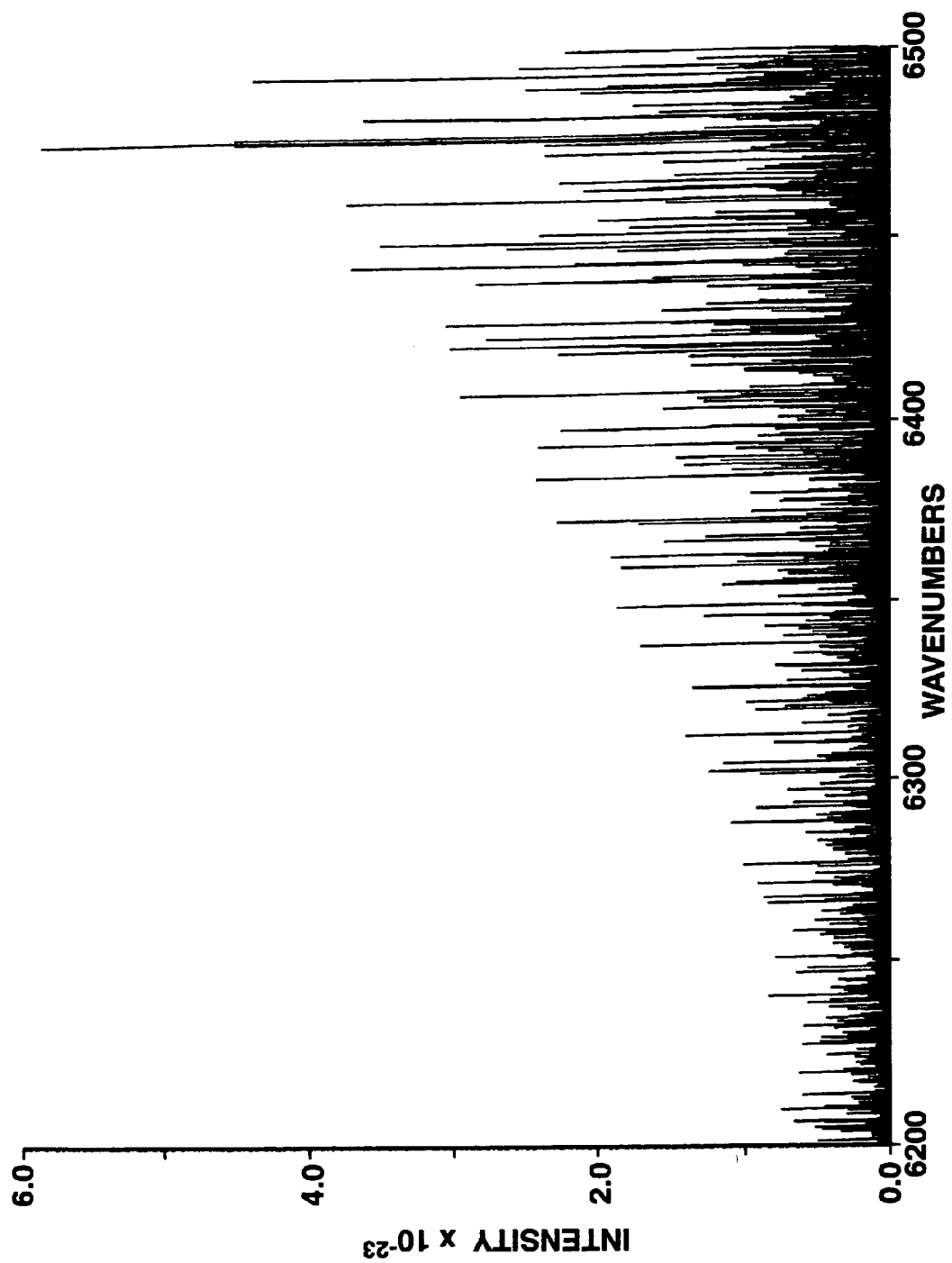
FIG. 6 is a graph of the U.S. Air Force's HITEMP modelling results for $H_2O$ at 1,500 K.
Figure 7:
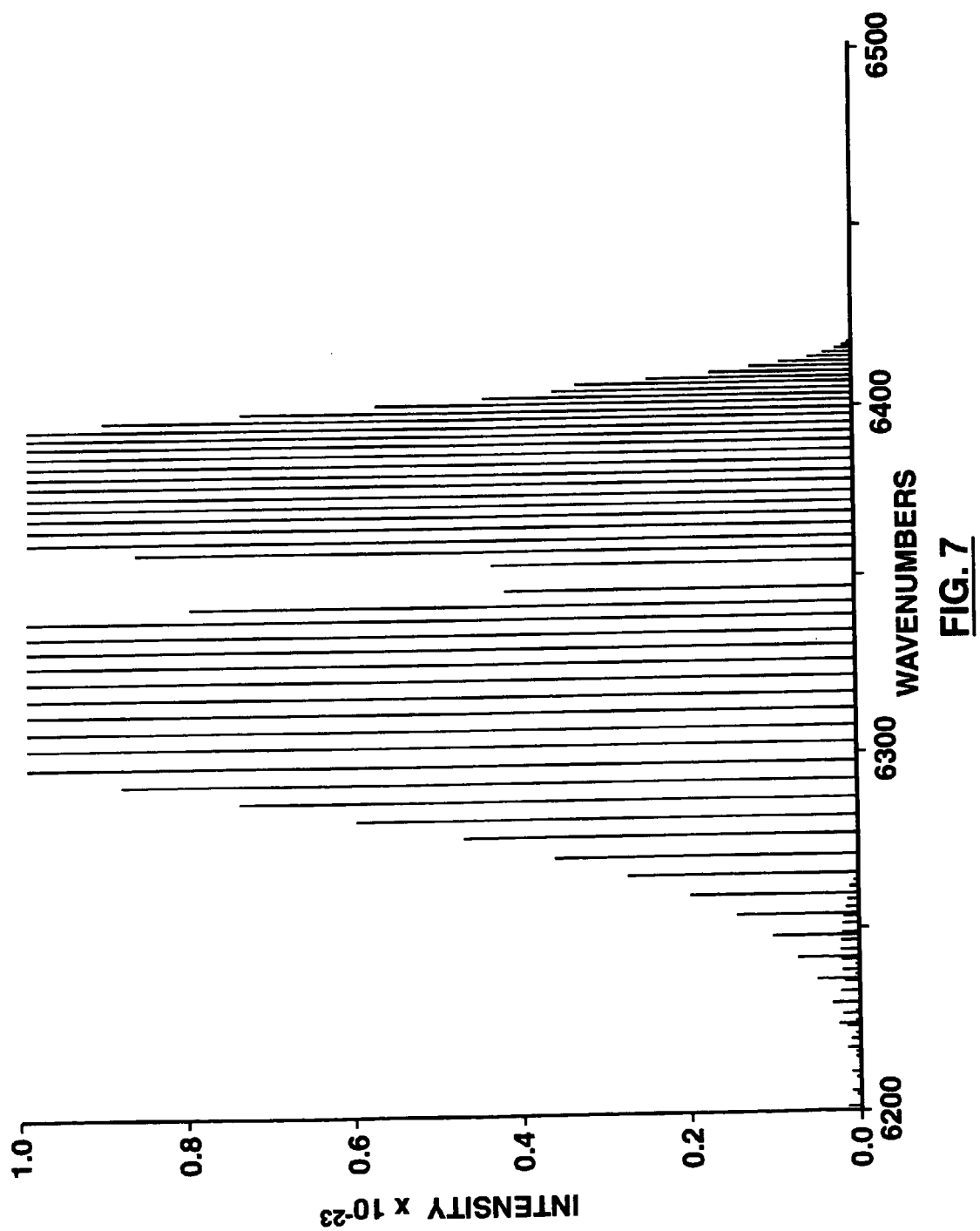
FIG. 7 is a graph of the U.S. Air Force's HITRAN modelling results for CO at 300 K.
Figure 8:
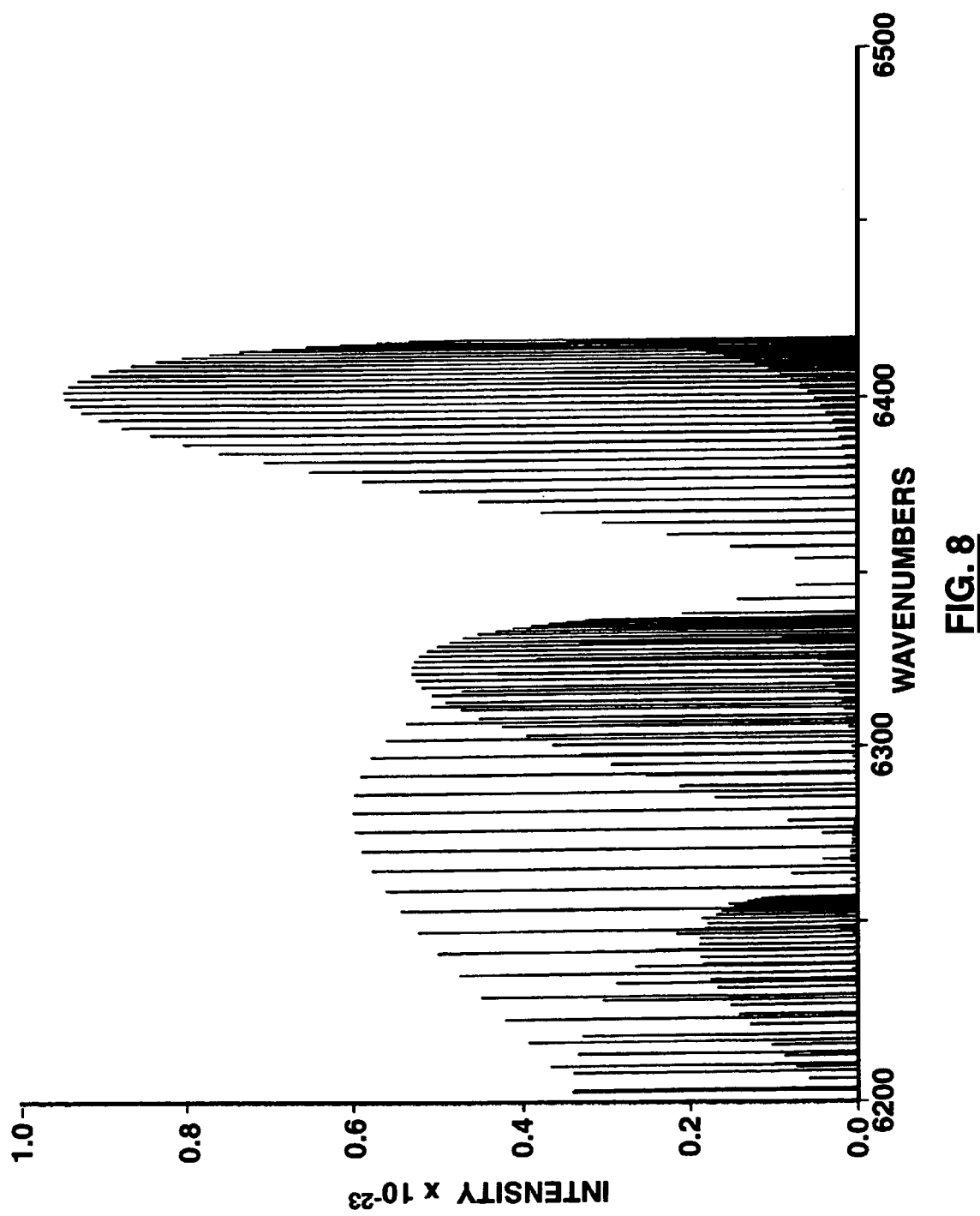
FIG. 8 is a graph of the U.S. Air Force's HITEMP modelling results for CO at 1,500 K.
Figure 9:
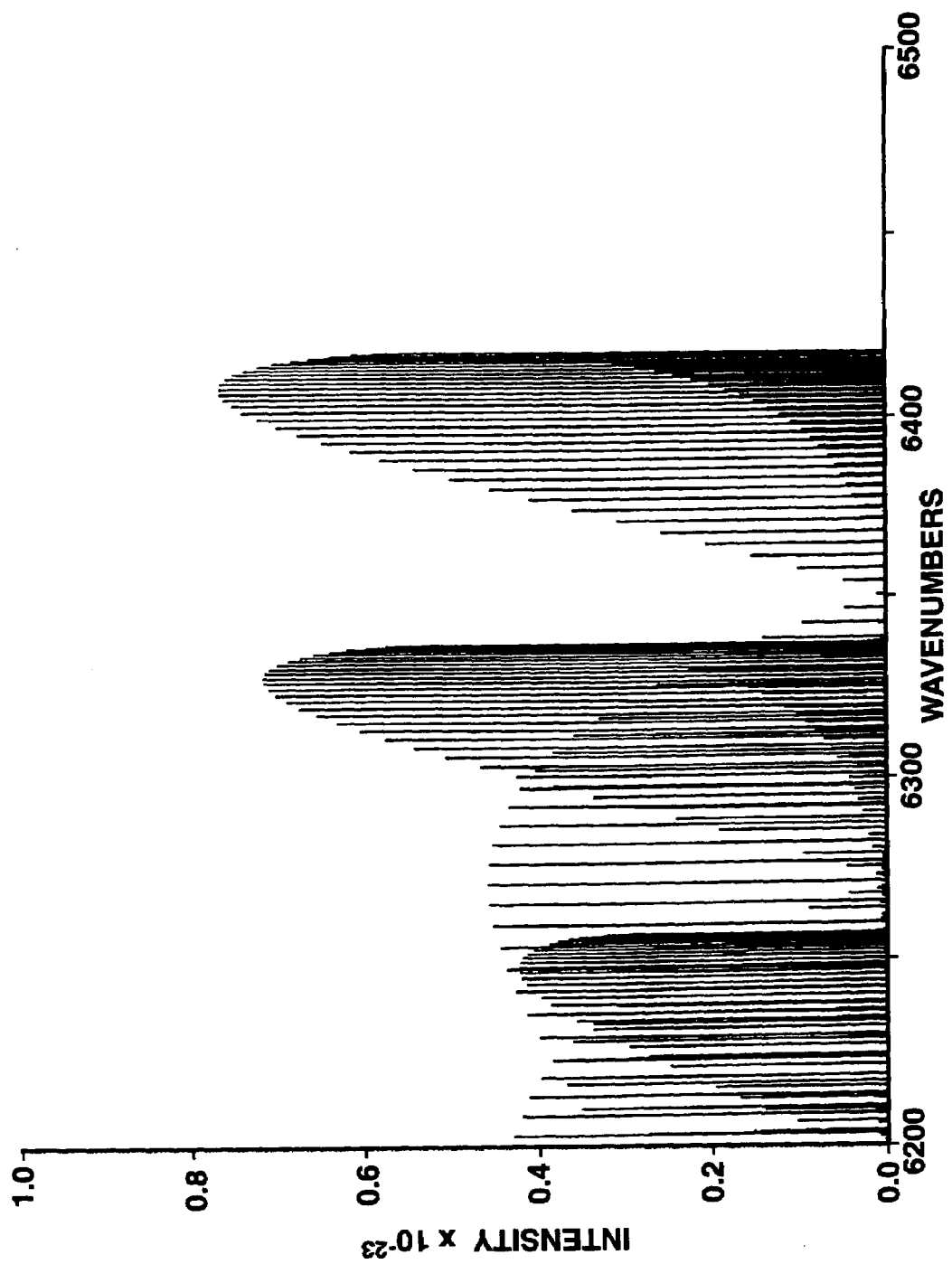
FIG. 9 is a graph of the U.S. Air Force's HITEMP modelling results for CO at 2,000 K.
Figure 10:
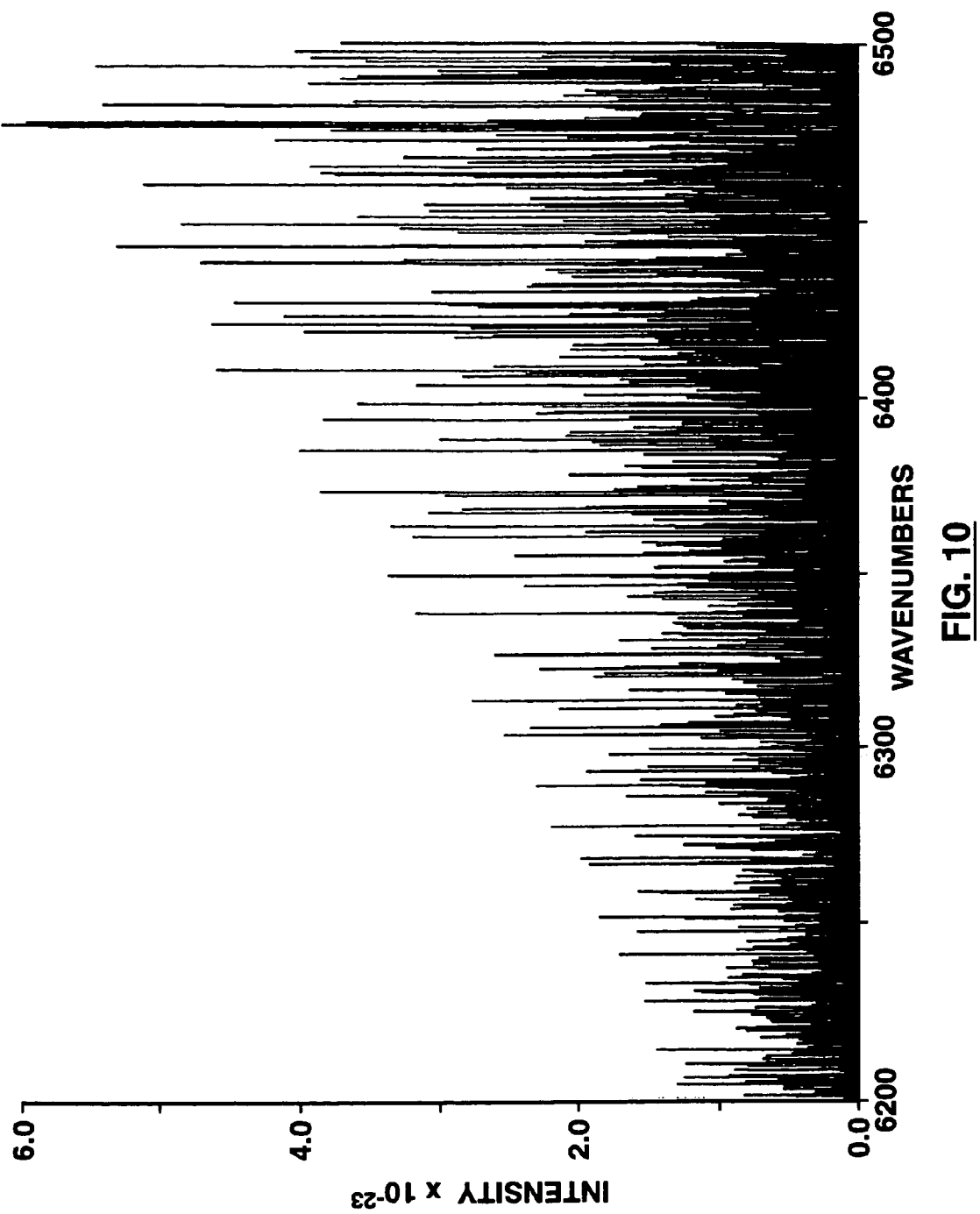
FIG. 10 is a graph of the U.S. Air Force's HITEMP modelling results for $H_2O$ at 2,000 K.
Figure 11:
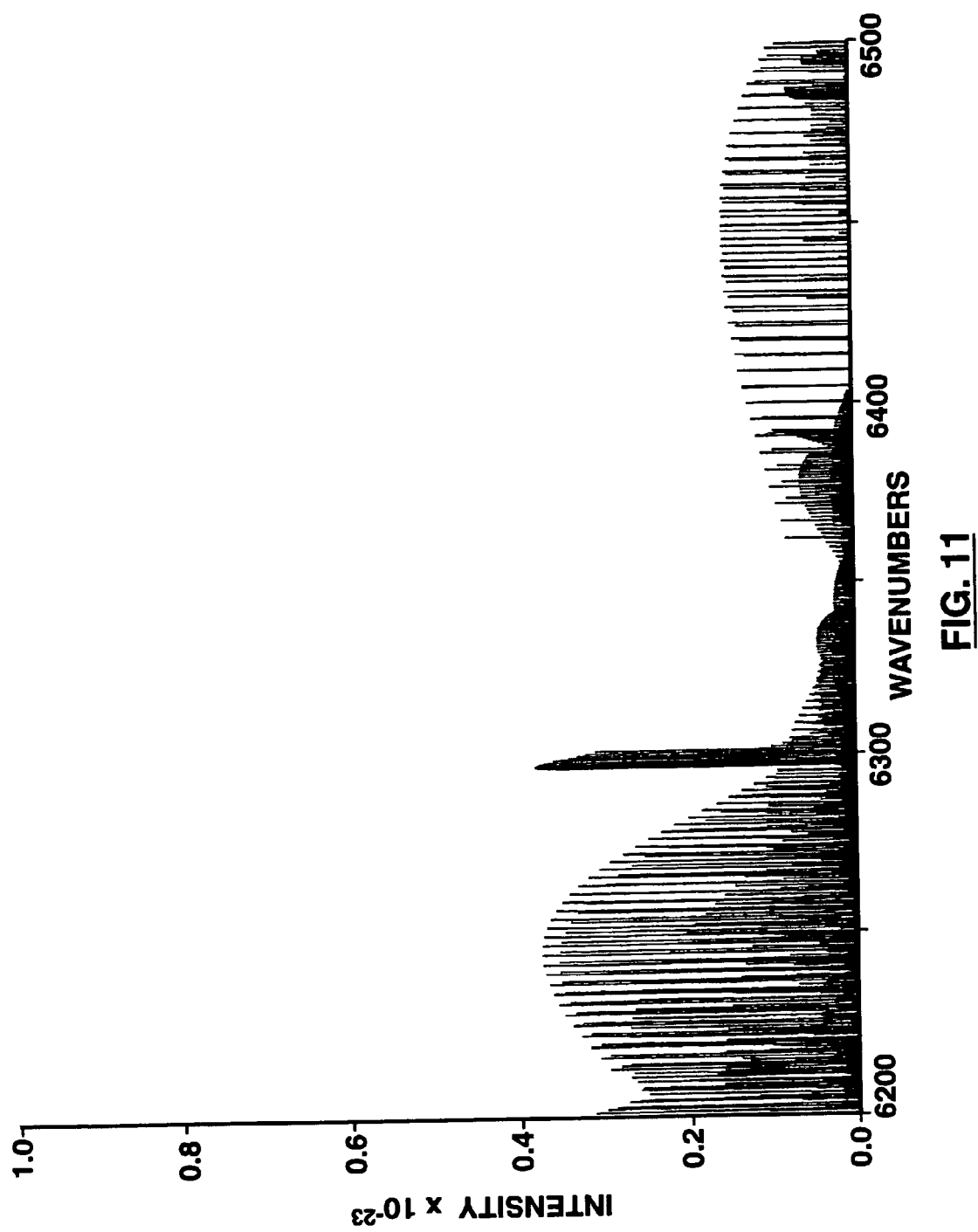
FIG. 11 is a graph of the U.S. Air Force's HITEMP modelling results for $CO_2$ at 2,000 K.

As previously noted, while there has been a great deal of spectroscopic work done at room temperatures, much less work has been done at elevated temperatures typically found in combustion applications, such as EAFs. In general, the locations and strengths of high temperature absorption features are completely independent of room temperature lines. One of the major difficulties in detecting CO and $CO_2$ at high temperatures is the dramatic increase in the strength and number of $H_2O$ absorption lines compared to room temperature. For example room temperature modelling results of optical absorption strengths are plotted for $H_2O$ in FIG. 5 over a range of wavelengths in the near infrared. FIG. 6 shows similar results for a temperature of 1500 K—clearly showing the increase in strength and frequency of the $H_2O$ absorption lines. FIG. 7 and FIG. 8 are similar to FIGS. 5 and 6, respectively, but for CO. Upon comparing FIGS. 5, 6, 7, and 8, it becomes apparent that CO lines are much less frequent and generally weaker than $H_2O$ lines. This is a limitation for CO, particulary due to the prevalence of $H_2O$ throughout the near infrared region. Therefore it is important to select not only a strong CO region, but also one where there is minimal $H_2O$ interference. However, there is uncertainty in $H_2O$ line positions and strengths at elevated temperatures. Accordingly, the selection process involves more of a dependence on $H_2O$ line strength and density trends, rather than exact positions. As a result, regions of relatively low $H_2O$ absorption but strong CO lines were considered the most attractive. FIGS. 9, 10, and 11, show HITEMP modelling of CO, $H_2O$, and $CO_2$, respectively, at 2,000 K. In particular FIG. 11 shows weaker $CO_2$ lines in the near-IR. As mentioned previously, research indicates even these weak predictions are much stronger than actual $CO_2$ absorption at elevated temperatures. Consequently, less consideration was given to choosing an optimal near-IR wavelength region based on $CO_2$ lines.

An available and affordable laser diode was then selected by looking at the several regions of equally attractive CO and $H_2O$ absorption characteristics. The laser diode selected based on the above results can access the approximate range of 6320–6340 $cm^{-1}$ (1577–1582 nm).

The first step in the laboratory tests was to compile a reference table (see Table 1) of laser current and temperature settings versus reference line locations. In combination with modelling results, this table provides a reference table to determine laser wavelengths. Once established, an approximate wavelength can be determined for each laser current and temperature setting. The location of the reference lines is more or less certain due to the high degree of independent validation of room temperature features for both CO and $CO_2$, which are both contained in the reference cell 54.

TABLE 1

| | Approximate Reference Currents (mA) for Various Diode Operating Temperatures | | | | | | | | | | | | | | | |
|---|---|---|---|---|---|---|---|---|---|---|---|---|---|---|---|---|
| Temp (° C.) | $CO_2$ #4 | CO #2 | $CO_2$ #5 | $CO_2$ #6 | $CO_2$ #7 and CO #3 | $CO_2$ #8 | $CO_2$ #9 | CO #4 | $CO_2$ #10 | $CO_2$ #11 | CO #5 | $CO_2$ #12 | $CO_2$ #13 | $CO_2$ #14 and CO #6 | $CO_2$ #15 | Date Conducted |
| 5 | 116 | 153 | 171 | 217 | 259 | | | | | | | | | | | May 1999 |
| 10 | | 87 | 110 | 165 | 212 | 254 | | | | | | | | | | May 1999 |
| 15 | | | 104 | | 161 | 209 | 252 | 265 | | | | | | | | May 1999 |
| 20 | | | | 99 | | 155 | 205 | 221 | 248 | | | | | | | May 1999 |
| 25 | | | | | | 93.5 | 153 | 171 | 202 | 247 | 272.5 | | | | | May 1999 |
| 30 | | | | | | | 85 | 108.5 | 146 | 196 | 226 | 241 | | | | Aug. 17, 1999 |
| 35 | | | | | | | | 83.5 | 145 | 180 | 197 | 242 | | | | Aug. 17, 1999 |

TABLE 1-continued

Approximate Reference Currents (mA) for Various Diode Operating Temperatures

| Temp (° C.) | CO₂ #4 | CO #2 | CO₂ #5 | CO₂ #6 | CO₂ #7 and CO #3 | CO₂ #8 | CO₂ #9 | CO #4 | CO₂ #10 | CO₂ #11 | CO #5 | CO₂ #12 | CO₂ #13 | CO₂ #14 and CO #6 | CO₂ #15 | Date Conducted |
|---|---|---|---|---|---|---|---|---|---|---|---|---|---|---|---|---|
| 40 | | | | | | | | | | | 126 | 145 | 196 | 238.5 | | Aug. 17, 1999 |
| 42 | | | | | | | | | | | 100 | 121 | 176 | 221 | 264 | Aug. 17, 1999 |

| | |
|---|---|
| CO #1 | 1576.628 |
| CO₂ #3 | 1578.939 |
| CO₂ #4 | 1577.362 |
| CO #2 | 1577.635 |
| CO₂ #5 | 1577.785 |
| CO₂ #6 | 1578.233 |
| CO₂ #7/CO #3 | 1578.669 |
| CO₂ #8 | 1579.105 |
| CO₂ #9 | 1579.567 |
| CO #4 | 1579.729 |
| CO₂ #10 | 1580.041 |
| CO₂ #11 | 1580.515 |
| CO #5 | 1580.828 |
| CO₂ #12 | 1581.003 |
| CO₂ #13 | 1581.578 |
| CO₂ #14/CO #6 | 1582.041 |
| CO₂ #15 | 1582.436 |

To obtain reliable high temperature data the best absorption line(s) were located experimentally. Since the locations and strengths of the high temperature features are, in general, completely independent of the room temperature lines that exist for the gases in the reference cell (namely, CO and $CO_2$), the first part of the lab work focused on finding suitable CO lines that were not significantly interfered with by water. First, the high temperature CO lines were conclusively located using pure CO as a fuel. The rich combustion of CO in air is shown below:

$$CO + x(O_2 + 3.78N_2) \rightarrow (1-2x)CO + (2x)CO_2 - 3.78(x)N_2$$

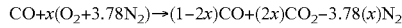

In a rich CO flame, substantial amounts of CO are present, with levels greater than 30% measured for some flame conditions. Off-gas temperatures obtained using CO as a fuel were in the range of about 1000 K to about 1500 K. Since $CO_2$ is also expected to be present in high levels for a CO flame, CO line locations were isolated from $CO_2$ by changing the reactant mix and observing the trends. In general, a richer flame should give off more CO than a leaner one. Once CO and $CO_2$ lines are differentiated, a comparison to high temperature modelling results is used to verify the final CO line locations. Such validation confirms the relative accuracy of CO modelling prediction in contrast to poor accuracy of $CO_2$ predictions.

Having established the high temperature CO profile, a pure $H_2$ flame is used to obtain the high temperature water spectrum in a similar manner. By combining the results of these two steps, locations of strong CO lines in combination with weak or non-existent water lines are identified.

After focusing on CO lines that are relatively removed from water lines, typical hydrocarbon fuels such as methane and propane, that produce a mixture of CO, $H_2O$ and $CO_2$ product gases, are used to confirm the superposition of pure CO and $H_2$ flame results to help find CO lines that appear to be relatively free of water interference.

It can be appreciated that certain laser settings such as the RF modulation, laser gain, and laser phase, are adjusted before any suitable CO lines are found amongst the backdrop of strong water lines. In early tests, the electronics of the laser were configured to give strong signals. This had the disadvantage of resulting in relatively large line widths so that saturation was occurring for many of the strong water lines. By adjusting the laser modulation to decrease the line width, line height is sacrificed. Eventually, a point appears to be reached where the line width no longer decreases, but below which the height continues to get smaller. The above procedure was conducted using the laser source 26 (from Unisearch Associates Inc., model number LCM-03). It was found that for this laser the following settings give the least possible interference, while maintaining reasonable signal strength to find as many CO lines as possible amongst the backdrop of strong water lines, namely: Gain=1700; Phase=1550; and RF=−2.15.

The Unisearch laser uses a thermoelectric cooler temperature-stabilized near-infrared diode laser (1.58 microns) as a light source to study CO and moisture at high temperatures as, for example, would exist in electric arc furnaces. In order to correctly determine the CO concentration the temperature of the furnace is monitored, and the line strength of the CO is adjusted accordingly. Moreover, if a 'clean' CO line to be monitored cannot be found at elevated temperatures (because of the presence of water lines that overlap the CO lines), the moisture level must be monitored and the CO signal corrected for the overlap with the water signal.

In order to measure the furnace temperature, two appropriate water lines that vary differently in line strength with the change in temperature can be monitored. Such a measurement can provide information on the furnace temperature as well as the moisture content. Since a ST/SL mode DFB lasers emit a specific wavelength of very narrow line width (compared to the line widths of the absorption signal of gases at ambient pressures and temperatures) when operated at a fixed temperature and current, the laser requires a rapid change of its operating parameters to scan multiple lines (CO and $H_2O$) virtually simultaneously.

Figure 18:
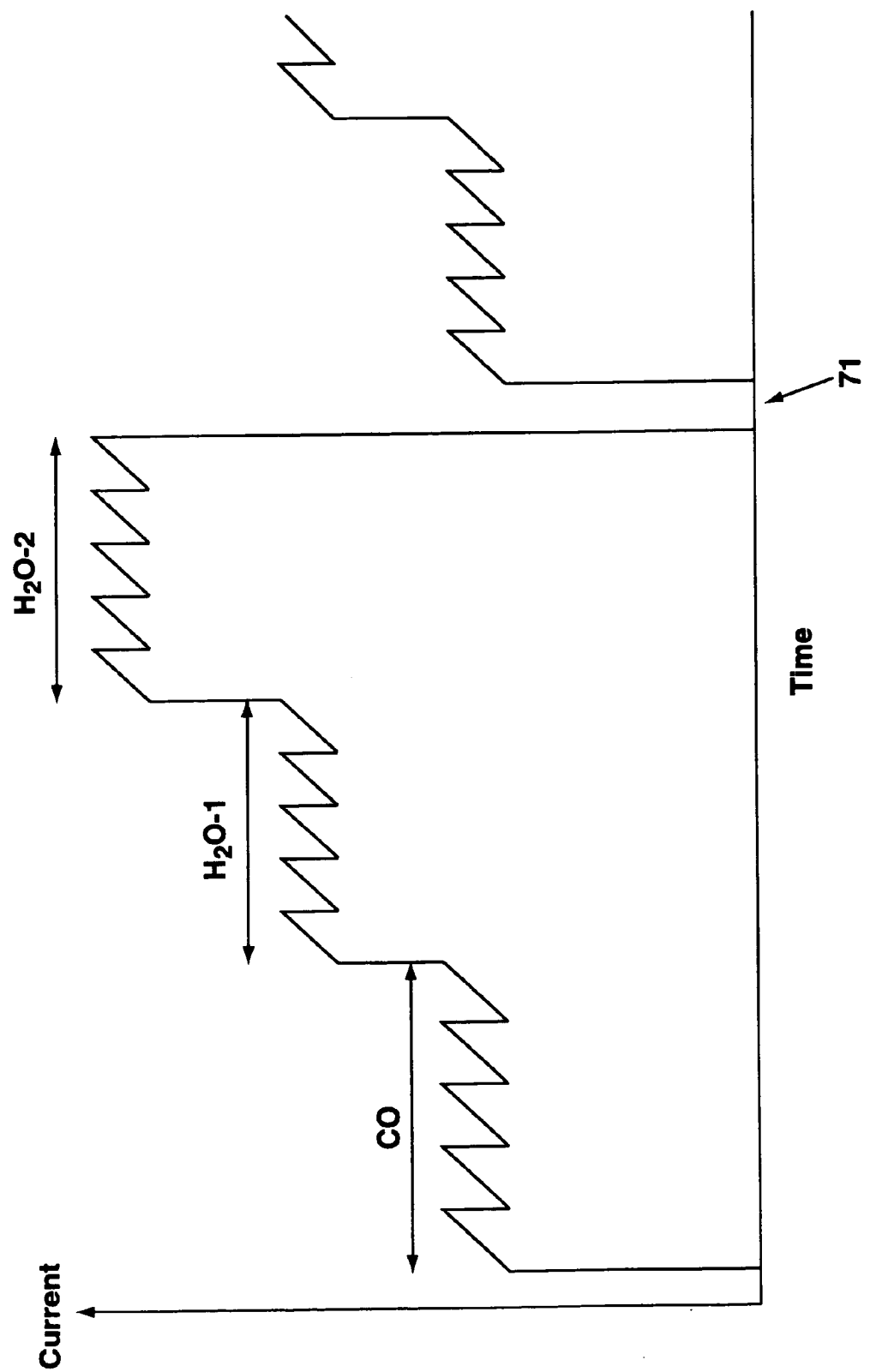
FIG. 18 is a graph of a laser scan.

In Unisearch's laser the temperature of the laser is held constant using a thermoelectric cooler. A constant DC current is applied to the laser that brings the emitted wavelength close to the absorption line of the gas. The laser current is rapidly and repeatedly swept across the absorption feature of interest (for example, a CO absorption line) for a certain period of time (usually a few milliseconds). The laser current is then jumped to another DC setting and rapid sweeps are made at this new current setting (for example, the first H$_2$O line to be monitored). Another jump in DC current and rapid sweeps could scan, for example, a second H$_2$O line being monitored. The ramp current with such jumps and sweeps is shown in FIG. 18.

Since the magnitude of the modulated signal of the gas detected at 2 f is proportional to the laser return power, it is important that the power be continuously monitored. The power varies from time to time due to the dust loading and the debris that crosses the laser beam. Also, the background radiation level from the arc in an electric arc furnace can be significant. A part of the background radiation from the arc that falls on the detector bandwidth is easily detected as well, along with the 'true' laser return power. This background radiation is monitored and subtracted to obtain the true power to compensate for the changing magnitude of the measured signal due to dust, debris and optical misalignment. In the current configuration, the laser current is switched "OFF" as at 71 for a very short period of time at the end of each integration cycle. The background radiation that is seen by the detector is measured during this period. The laser is then switched "ON" and the scan continues.

Figure 19:
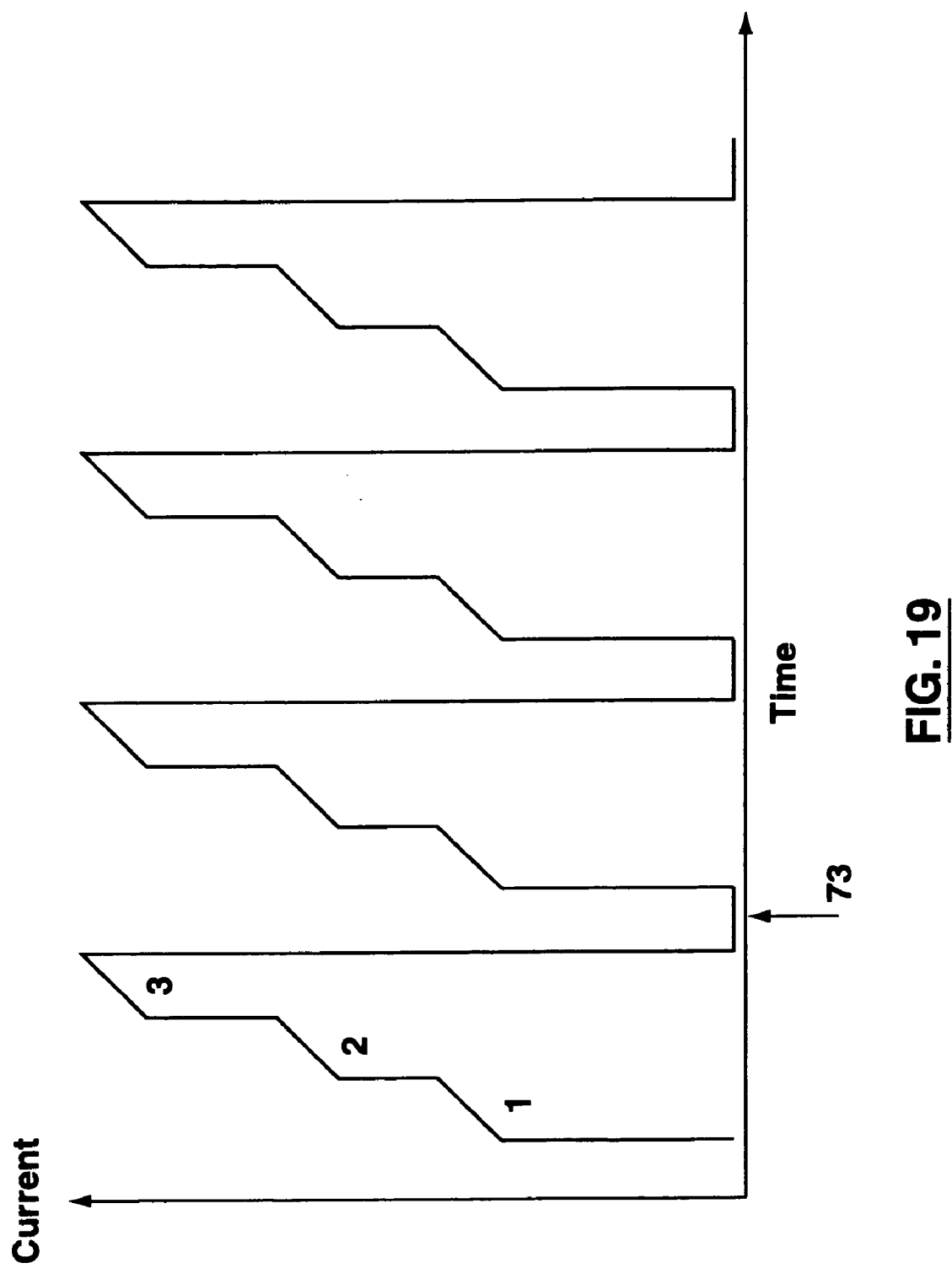
FIG. 19 is a graph of an alternative laser scan.

A variation of the scan is shown in FIG. 19. Here, the species 1 (CO) is scanned first (single sweep), the current is jumped to the next DC value, species 2 (H$_2$O-1) is scanned (single sweep) and the current is again jumped to the next value where species 3 (H$_2$O-2) is scanned (single sweep). The laser current is then switched "OFF" as at 73 and the background radiation measured. The laser is then switched "ON" and the scan continues.

Operating the laser in a 'jump-scan' mode to monitor multiple species can be essentially simultaneous. The Unisearch laser analyzer is set to make a single sweep in about 4 milliseconds. Therefore, all the three species and the background radiation can be monitored about every 15 milliseconds.

Once several attractive CO lines are located, the choices are further narrowed. In particular, closely controlled tests are conducted for various air-to-fuel (A/F) ratios using propane and methane, with the lower A/F ratios resulting in increased CO production. From these tests, preliminary calibration curves can be plotted, such as that illustrated in FIG. 13. Since absorption strength is a strong function of temperature for many of the lines investigated, it is important at this stage to isolate temperature effects from concentration effects. The easiest way to accomplish this is to maintain a constant temperature in the flame region, for all A/F ratios. Since the A/F ratio has a significant impact on flame temperature (in addition to CO concentration), this requires using independently controlled inputs of O$_2$ and N$_2$, rather than being limited to a fixed ratio of the two in the form of air. For example, to generate increased CO in the off-gas, the oxygen/fuel ratio must be reduced to allow richer combustion. However, since the temperature will otherwise decrease when moving away from stoichiometric conditions, a concurrent reduction in the level of dilution gas (nitrogen, N$_2$), accomplished by a reduction in the N$_2$/F ratio, will allow for constant temperature control.

The thermocouple cannot be in the measurement region while the optical measurements are being conducted since the laser beam path would be interrupted. Since refined temperature measurements are not critical at this stage of testing, the thermocouple is left in a fixed position just above the maximum extent of the optical beam path, as confirmed with the visible alignment laser. On the basis that a fixed flow rate of reactant gases will result in an approximately constant flame plane height 25 and roughly equal convection to the thermocouple for a given fuel, the flame plane temperature is assumed to be lower than the thermocouple measurement by a fixed amount, independent of the O$_2$/F ratio. In other words, it is assumed that for a fixed flow rate of influent gases, if the thermocouple temperature is the same from one O$_2$/F value to another, then the temperature in the measurement region itself is also constant. This provides an empirical and iterative process for obtaining the influent gas settings that allow measurement of a wide range of suitable CO off-gas concentrations, with temperature held more or less constant.

To aid in the first guess at rotameter settings that result in a range of CO levels over a constant temperature, adiabatic combustion is assumed to plot influent gas mixtures of various O$_2$/F and N$_2$/F levels versus adiabatic flame temperature, all of which can be predicted by software programs, such as STANJAN, and later plotted in an appropriate graphing application, such as Microsoft Excel. Levels along a particular isotherm are chosen as the first iterative step and subsequent adjustments are made to these settings to obtain actual thermocouple temperatures closer to one another than the adiabatic assumption produces.

It is noted that the accuracy of the above assumptions is reduced by several factors, including the assumption that flame height depends only on reactant gas flow rate and not composition, the fact that constant influent gas flow does not mean constant exhaust gas flow (due to both increased off-gas temperature and unequal moles of reactants and products), and the fact that convection is not constant due to both of the above factors in addition to differences in heat capacities associated with the variable off-gas mixture.

Once the rotameter settings are determined for a given gas, the levels of exhaust gases are measured extractively using a high range detector. To save time only one measurement was obtained for each gas setting regardless of how many subsequent tests were conducted for each condition. The off-gas concentrations obtained extractively are converted from a dry basis to a wet or actual basis using the following formula:

$$\text{Actual}[\,] = \frac{\text{Dry}[\,]}{1 - \% \text{ H}_2\text{O}} \quad (2)$$

Where the Dry [ ] represents the extractive instrument reading and the % H$_2$O is approximated using STANJAN (since no extractive value can be obtained).

Optical measurements are then taken for each of the promising CO lines, using the pre-set reactant gas flow rates. In this manner, curves of peak height can be plotted for each of the flame conditions (and resultant CO concentrations) and the response then assessed. Using the CO concentrations obtained with the extractive probe, and corrected for water content, a plot of peak height versus CO concentration is then plotted, for example, see FIG. 13.

An ideal response is a graded increase in CO peak height for each successively increasing extractive CO measurement. In addition, the shape of the CO line for pure CO should match that for hydrocarbon fuels such as, for example, CH$_4$ and propane (see FIG. 12). If the width does not fit the pure CO line well at a comparable temperature, then this is an indication of interference from neighbouring water lines. Further confirmation of water interference is obtained by plotting a line in the same spectral region using pure H$_2$ fuel. If this water line is flat or nearly flat, it can be assumed that water is not present in this region, at least for the given flame temperature. If this water line is flat and of zero magnitude, the CO calibration curve for the hydrocarbon fuel will intersect zero. Finally, water interference can be assessed by confirming the independence of results for different fuels, since the combustion of fuels such as methane and propane produce significantly different amounts of water in their product gases. In general, water production is proportional to the H/C ratio of the hydrocarbon fuel. Therefore, $CH_4$ produces a greater proportion of water than any other hydrocarbon fuel.

A good CO response for one temperature does not automatically mean the response is acceptable across the entire range of desired temperatures of about 1000 K to about 2000 K. This is due to the change in intensity of absorption lines with temperature. Therefore the above procedure is repeated on a subset of CO absorption lines that were attractive at the initial temperature evaluated. This procedure can eliminate some of the CO lines that were attractive at the one temperature but would not work well across the full temperature range.

Having selected the optimal CO absorption line, the water lines are then located. Selection of water lines can be an easier task than finding CO lines unaffected by water due, in part, to the frequency and strength of water absorption in this optical region. Assuming temperature is known, only one water line would be required to obtain concentration. However, the ratio of peak strengths for two water lines must be used to optically obtain the temperature, since thermocouples are not suitable for EAF applications. The following should be considered in selecting the water lines:

Strong spectroscopic line(s) for water over the full range of temperature conditions ($\cong$1000–2000 K);
Minimal interference with other species;
Lines are accessible within the jump scan range of the laser; and
Two water lines that respond differentially to changes in temperature.

Due to the tremendous strength and frequency already demonstrated for water lines, the first two factors are not a problem. The last point limits the range of the laser to a smaller range represented by the limits accessible by jump scanning using current alone. Jump scanning involves a limited portion of the current tuning only range. For the Unisearch laser as used for this experiment, the maximum jump scan range is somewhere in the neighbourhood of 40–50 mA, representing a maximum search range of approximately 0.5 nm from the optimal CO line.

Within this range, then, the search for $H_2O$ lines focuses on locating lines that respond differentially to changes in temperature. Optical temperature sensitivity is maximized when two lines are used from completely different absorption bands that respond in completely opposite directions to temperature, for example, optimal sensitivity can be achieved when one of the two water lines increases with increasing temperature while the other decreases. It can be appreciated, however, that both lines must be measurable over the entire temperature range.

Once two water lines are found that best meet these requirements, they are used as optical temperature measurement tools. Several flame conditions (using different fuels, such as, for example, methane and propane) are tested to evaluate the change in the ratio of peak height of these two lines with changing temperature, as measured by the thermocouple.

After locating optimal CO and $H_2O$ lines, increasingly accurate calibration curves are developed. Multiple regression tools (for example, the ones available in Microsoft Excel) are used to evaluate large data sets that encompass a wide range of concentration and temperature tests for each surrogate fuel. Since multiple regression can evaluate both temperature and concentration effects concurrently, it is no longer necessary to confine influent gas flows by the constant off-gas temperature and flow requirements. However, it is critical to obtain representative and accurate data for each measurement. In addition, accurate calibration curves depend on a large data set.

The Unisearch laser of this experiment is used to record peak attributes for CO and the two water lines, such as, for example, the best of peak height, peak area, or other suitable peak attributes, as determined through statistical analysis. This data is used to optically assess temperature and concentration.

Figure 17:
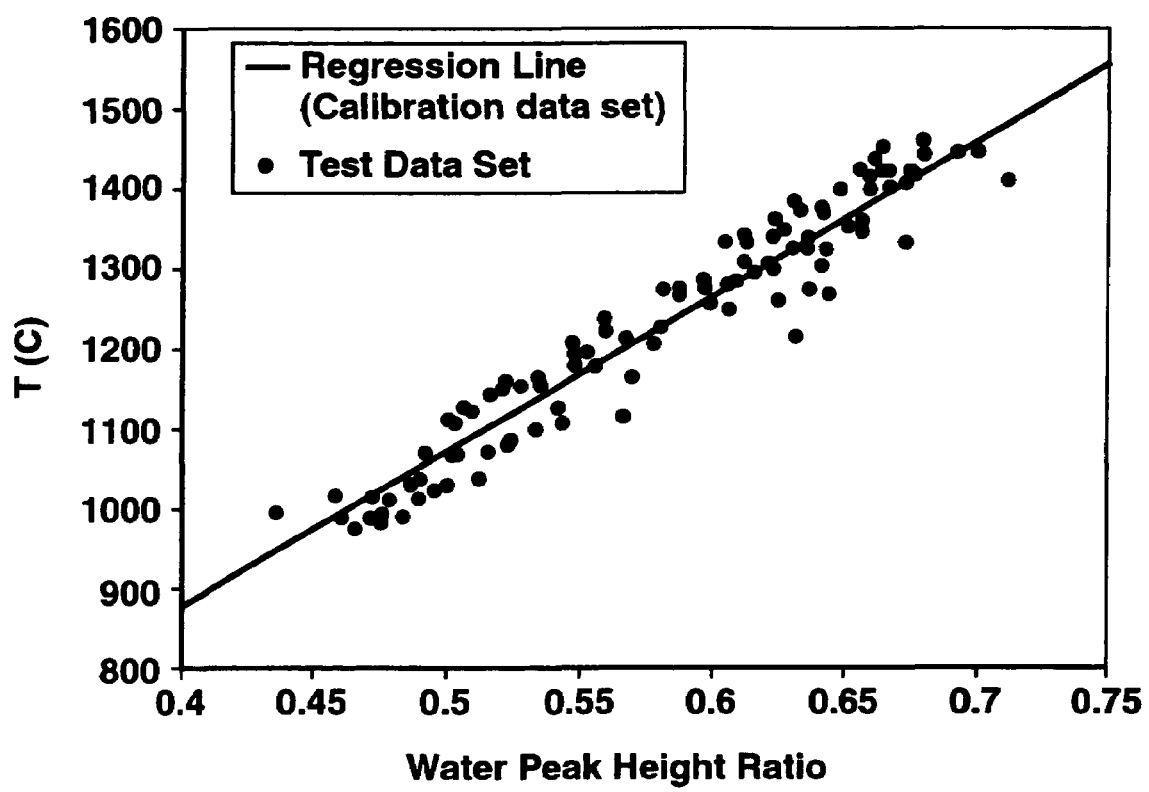
FIG. 17 is a graph of a comparison of the gas temperature calibration curve with test data ($H_2O$ peak height ratio versus temperature)

To assess the temperature optically for a given fuel, the ratio of the selected peak attribute for two water lines is fit against several higher order polynomials. The optimal combination of fit and minimal complexity is then used to describe the temperature-peak attribute ratio relation. An example of a 7th order polynomial fit against peak height ratio for two water lines is given in FIG. 17.

Calibration of the selected CO peak attribute as a function of temperature and concentration is accomplished in the lab via multiple regression against extractive and thermocouple data. Since $H_2O$ concentrations are not attainable with extractive samplers, assumptions must be made to enable the correction of dry CO readings to actual CO concentrations (as per the earlier equation). In addition, the lack of independent $H_2O$ confirmation necessitated the use of the calculated values to establish the multiple regression for $H_2O$ peak attribute as a function of temperature and concentration. As a result of this increased uncertainty in actual $H_2O$ concentration, the values of $R^2$ (a statistical measure of the error) are expected to be larger for optical determination of $H_2O$ concentration than they are for CO concentration, since the effects of the $H_2O$ estimate on CO concentration are limited to the amount of the correction from dry to wet concentrations.

In order to estimate the $H_2O$ concentration, a mass balance approach using rotameter inflows is necessary, along with a consideration of the water gas shift equilibrium, which is very significant under rich conditions. The following equations were solved for $CH_4$ (slight modifications to the values are necessary for other hydrocarbon fuels due to the different number of carbon and hydrogen atoms) to obtain an estimate of the $H_2O$ concentration:

$$nC = nCH_4 = n_T(yCO_2 + yCO) \quad \text{Equation 1}$$

$$nO = 2*nO_2 = n_T(2*yO_2 + yH_2O + 2*yCO_2 + yCO) \quad \text{Equation 2}$$

$$nH = 4*nCH_4 = n_T(2*yH_2 + 2*yH_2O) \quad \text{Equation 3}$$

$$1 = yN_2 + yCO + yCO_2 + yH_2 + yH_2O + yO_2 \quad \text{Equation 4}$$

$$N_2 = n_T * yN_2 \quad \text{Equation 5}$$

$$CO_{(g)} + H_2O_{(g)} \_ CO_{2(g)} + H_{2(g)} \quad \text{Equation 6}$$

$$K_p = \exp[\Delta G^0_T / (R_u T)] \quad \text{Equation 6a}$$

$$\Delta G^0_T = \Sigma V_i g^0_{f,T} \quad \text{Equation 6b}$$

$$yCO = X_{CO}(1 - yH_2O) \quad \text{Equation 7}$$

Where:
nX=molar inflow of reactant gas X through the rotameters (obtained from rotameter calibration chart) [moles]

yX=mole fraction of product gas X in the off gas
$n_T$=total product gas (exhaust) flow [moles]
$K_p$=equilibrium constant
$\Delta G^o{}_T$=standard Gibb's function change [J]
$R_u$=universal gas constant [8.314 J/(mol*K)]
T=temperature [K]
$v_1$=moles of component "i" from balance chemical equation
$g^o{}_{f,t}$=Gibb's function of formation [J/mol]
XCO=Dry concentration of CO (extractive reading)

Dilution from the shroud flow ($N_2$) into the combustion region were considered using an iterative approach based on "Equation 1." Wherever CO and $CO_2$ extractive data are available (i.e., not off scale for the extractive device), any apparent deficiency between the inflow of C moles (from the fuel) and the outflow in the form of CO and $CO_2$ is caused by some shroud nitrogen penetrating to the extractive measurement location. Quantification of this dilution and correction of the predicted concentrations allows increasingly accurate predictions to be made.

To further improve temperature and extractive sampling accuracy the thermocouple and sample probe measurements are conducted at the same point where optical measurements are obtained. While significant variation in temperature and concentration is expected in the measurement region, single measurements in the middle of the measurement region are used to obtain "average" values. Ideally, multiple measurements are taken throughout the region to obtain an even more representative temperature and concentration profile. Since the thermocouple and extractive probe will block the laser beam when placed in the measurement region, an accurate and repeatable method must be used to move the thermocouple and probe into the same position each time measurements are taken. To accomplish this the probe and thermocouple were attached at the same position to a vertical kinematic stage to ensure reproducibility of the measurement location. One temperature and extractive measurement is taken either before or after each optical test.

Figure 12:
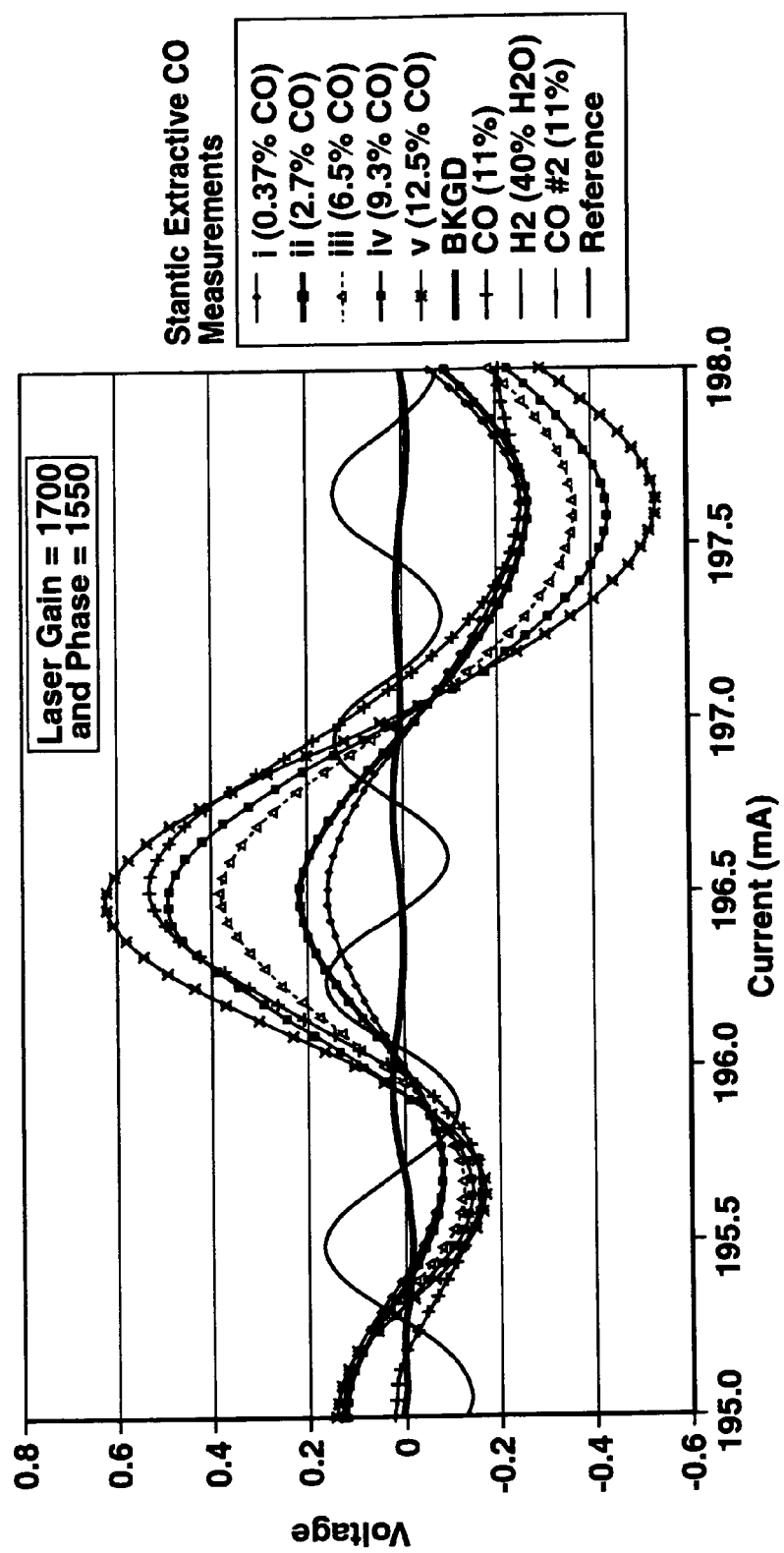
FIG. 12 is a graph of an optical response for an optimal CO line.

Optical results for the most attractive CO line in the measurement region accessible by this laser are shown in FIG. 12. These measurements were obtained using methane as a fuel with thermocouple temperatures of about 1550 K. Pure CO was also used as a fuel for comparison purposes. Several things worth noting include the exact matching of the methane profile with the pure CO flame width to the left of the peak. To the right of the peak there is some difference due to superposition with the tail of a small $H_2O$ peak (the left side of the peak is somewhat visible at the right edge of the graph). This indicates minimal interference with water.

By using experimental absorption measurements over a wide range of representative gas conditions it was determined that the CO absorption line located at 1577.96 nm was the optimal CO feature present within the 1577–1582 nm operating range of the selected laser. The optimal water absorption lines were 1577.8 nm and 1578.1 nm. FIG. 12 shows increasing absorption peak height with increasing CO concentration under roughly isothermal test conditions.

An analysis of the method's accuracy has been conducted using 209 calibration and 105 unique test burner setpoints. The burner setpoints had a random distribution across CO concentration (from 0 to 10%) and gas temperature (from 970 to 1480° C.). The water concentration varied from 3 to 27%. The calibration data set and multiple regression analysis provided calibration curves linking the absorption peak heights with measured gas concentrations and temperatures. The test data set was used to independently evaluate accuracy. It was found that peak height gave a slightly better correlation with CO concentration than did peak area. The CO concentration increased linearly with CO peak height. There was a weak dependence on temperature. A small correction for the water concentration was required. The multiple regression analysis provided a calibration curve of CO concentration as a function of the CO and water peak heights. The correlation had an R squared of 0.96, indicating excellent representation of the data.

Figure 13:
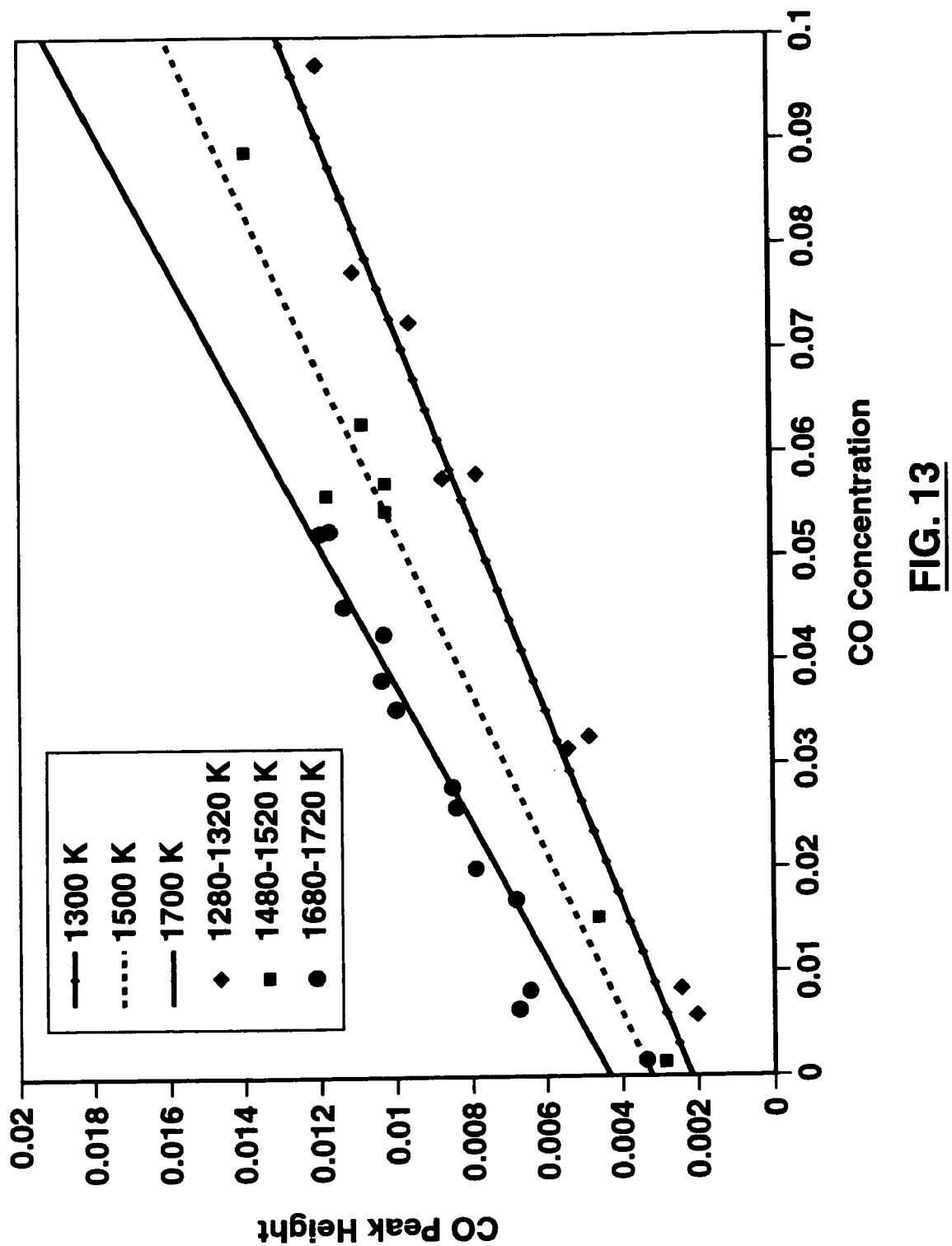
FIG. 13 is a graph of a comparison of an isothermal CO calibration curve with test data.

FIG. 13 compares the CO peak height to the measured CO concentration for groups of data that had temperatures within a ±20° C. range. The isothermal calibration curves are also shown. These results show that the CO peak height response is essentially linear with CO concentration, with a slight offset attributed to a weakly interfering water absorption line nearby. An error analysis using the previously established calibration curve and the test data indicates that this optical technique is able to measure CO concentrations within a standard deviation of 0.47% CO. This value is comparable to the accuracy of extractive systems and is considered to be satisfactory in light of the high CO concentrations present in many EAFs, where levels in excess of 20% CO are common.

The gas temperature increased linearly with the ratio of the water peak heights. The multiple regression analysis determined a calibration curve with an R squared of 0.92. FIG. 6 shows the variation of the selected water peak height ratio with temperature. The test data analysis found a standard deviation of the error of 36° C. The use of two separate lasers to access more widely separated water lines is likely to improve temperature measurement sensitivity considerably.

There were numerous difficulties pertaining to the measurement of $CO_2$ at the desired temperatures. Unlike CO, the absorption peaks were very weak at elevated temperatures for this gas in most areas of near-IR, including a specific region selected. Combined with the increase in $H_2O$ peak strength and intensity, this made $CO_2$ measurements difficult in the initial test range. Using HITEMP modelling results, it became apparent that an alternate region in the near-IR contained some strong $CO_2$ lines that appeared to be sufficiently far away from neighbouring $H_2O$ lines for temperatures from about 1000 K to about 2000 K. A more promising region for high temperature $CO_2$ measurements is around 2.0 µm.

Figure 14:
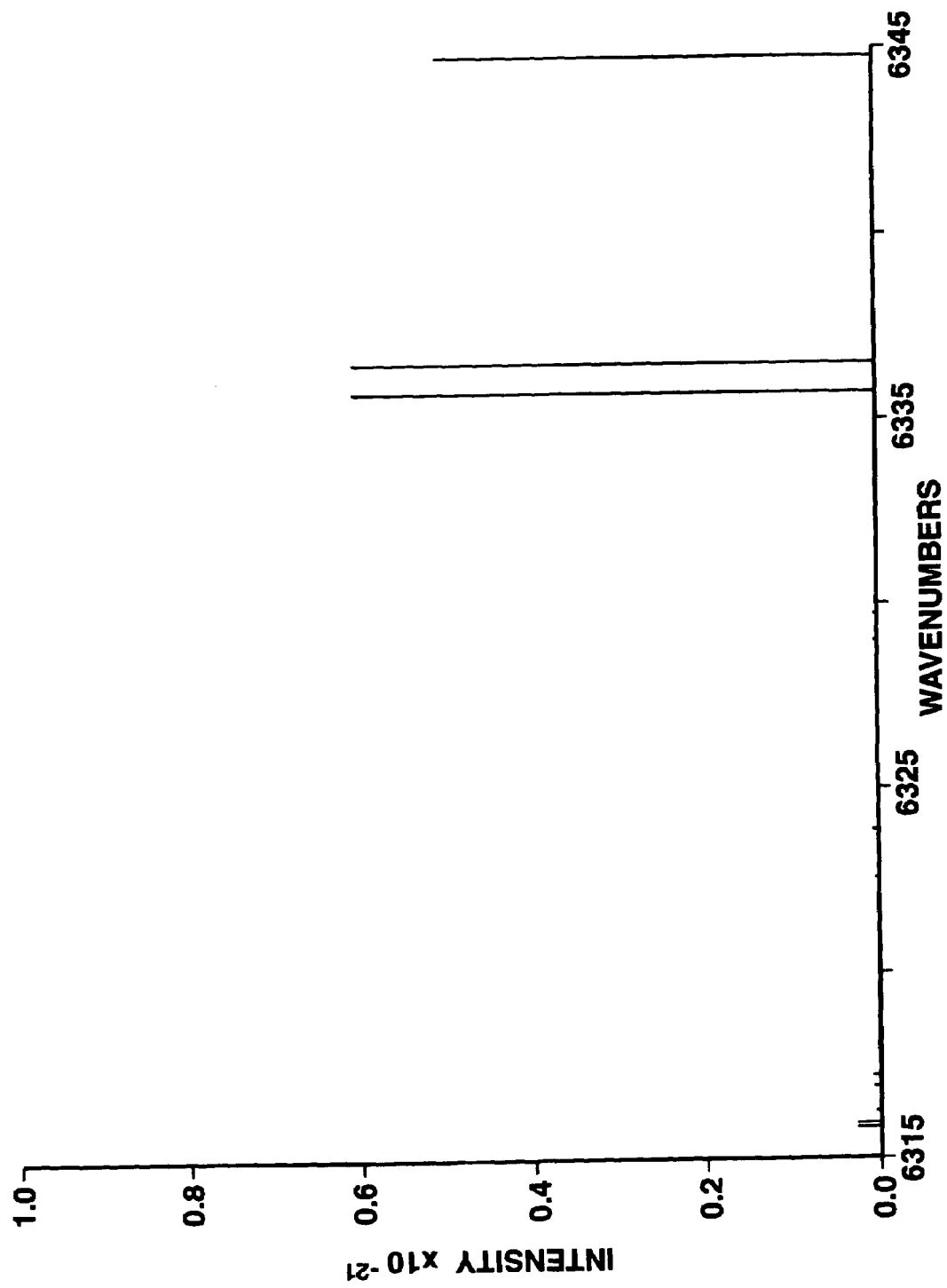
FIG. 14 is a graph of HITRAN modelling results for OH at 1,500 K.

It was discovered during this experiment that two particularly strong OH absorption lines were readily accessible within the jump scan range of the selected CO peak. The approximate locations of these two lines were confirmed by HITRAN modelling results, as shown for 1500 K in FIG. 14. While these two lines are very close together, it is not possible to use their ratio for temperature determination. One reason is that they appear to move very much in sync over a wide range of temperatures.

Application to an Electric Arc Furnace

Figure 15:
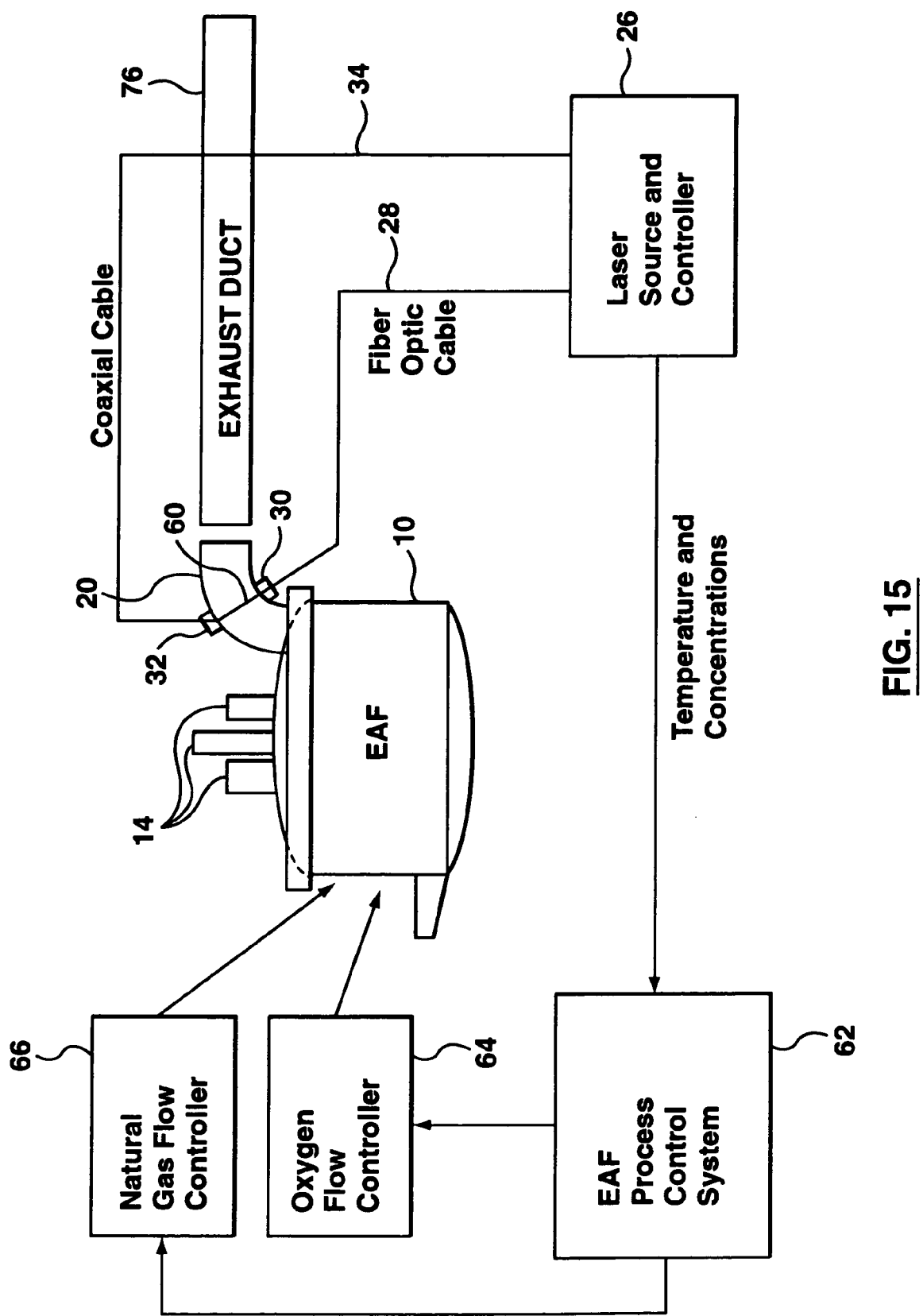
FIG. 15 is a schematic view of an optical measurement system of this invention used in an electric arc furnace.
Figure 16:
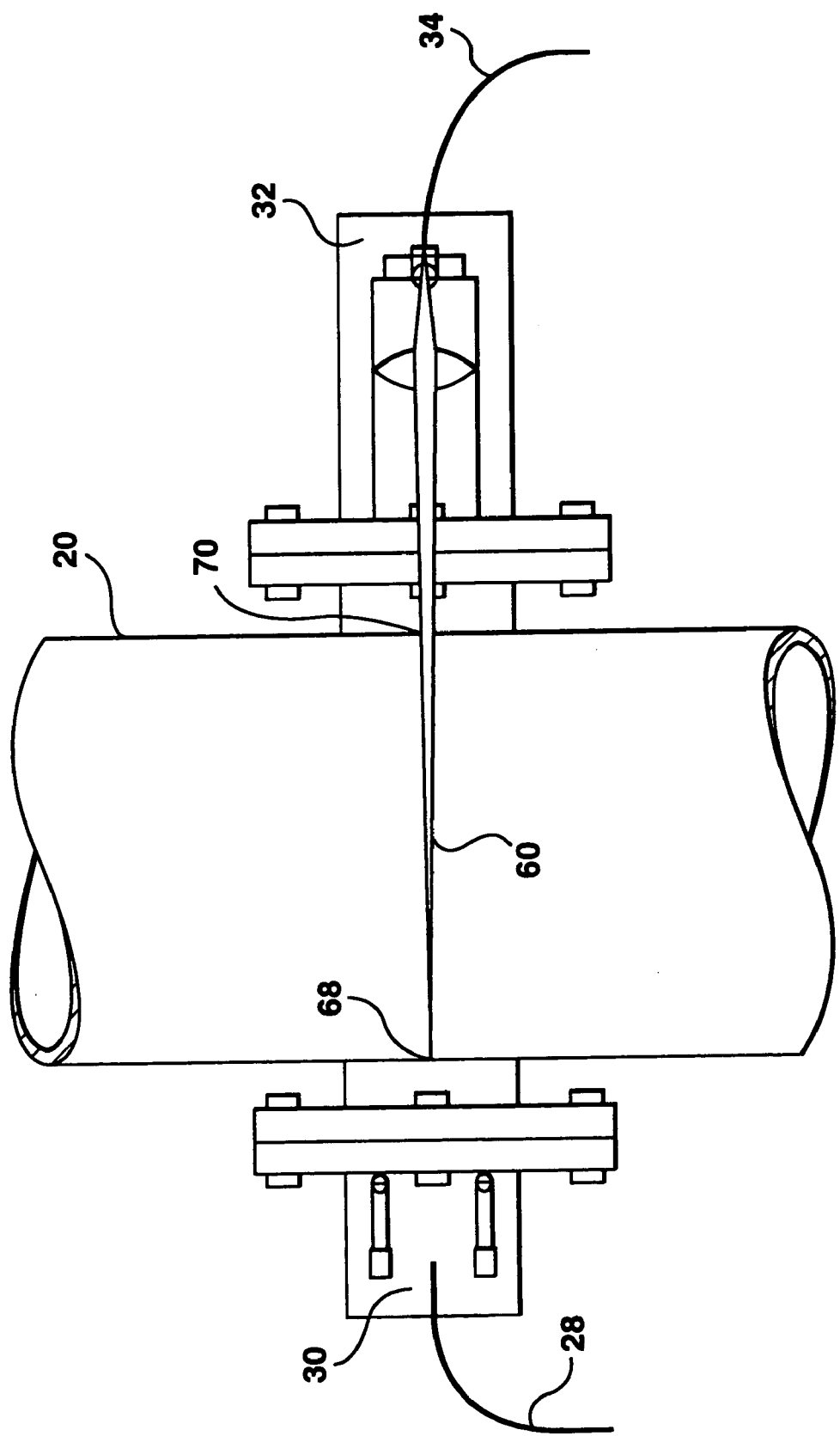
FIG. 16 is a schematic view of the optical system in an exhaust duct of an electric arc furnace.

A schematic of an EAF system using the process sensor of this application is shown in FIG. 15. A more detailed view of the exhaust duct is shown in FIG. 16. In general FIG. 15 shows an EAF 10 having an exhaust duct 20. A laser source 26 is provided to transmit a laser beam through fibre optic cable 28 to a launcher assembly 30 (see FIG. 16). The laser beam is transmitted across duct 20 as at 60 to detector 32 which, in turn, transmits an appropriate electronic signal back to source 26 via a coaxial cable 34. It can be appreciated that a fiber optic cable can also be used in place of coaxial cable 34. Source 26, through use of a computer that can be located on-board (for example, see FIG. 4) uses the calibration curves calculated for high temperature applications to interpret the readings of the concentration of, for example, CO, from detector 32 and sends an appropriate signal to an EAF process control system 62. Control system 62 can then adjust the oxygen flow through controller 64, or temperature of the EAF through, for example, natural gas flow controller 66, as needed. FIG. 15 illustrates a process control system that uses real time sensors to obtain selective measurements of the off-gas constituents and provides adjustment of the inputs to a furnace (such as oxygen, fuel, electric power, etc.) on a continuous feedback loop.

Although the laser beam propagates through the measurement path 60 in the exhaust duct 20, small holes 68 and 70 in the duct allow the laser launch assembly 30 and detector 32, respectively, to be located away from the harsh conditions within the exhaust duct. Accuracy concerns can arise, however, due to the in-leakage of room air through the small holes 68 and 70. It is expected that the contribution of ambient gases to the measured signal strength should be negligible, however. This is principally related to the fact that the high temperature optical absorption wavelengths selected have no significant room temperature absorption for species likely to be present in the steel plant ambient air, according to HITRAN modelling results. Moreover, any dilution of stack gases by the relatively small inflow of ambient air can be further minimized by designing the optical interface in such a manner that ambient air is largely directed at an angle downstream into the stack beyond the measurement zone.

Figure 15A:
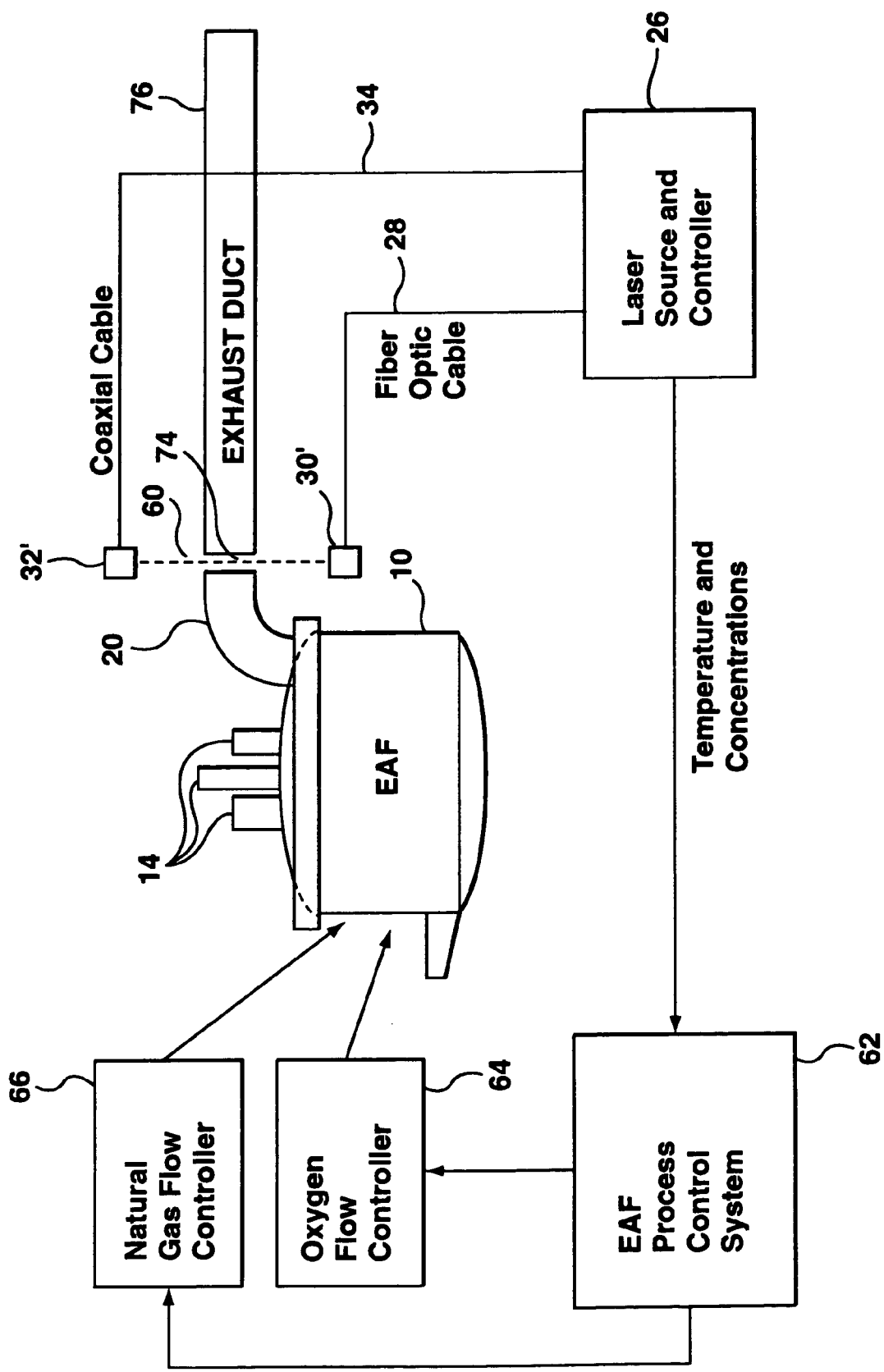
FIG. 15a is a schematic view of an alternative optical measurement system of this invention used in an electric arc furnace.

A schematic of an EAF system using an alternative process of this invention is shown in FIG. 15a. Except where noted and described below the same reference characters will be used to identify the same parts in both figures. In FIG. 15a the launcher assembly 30' transmits the laser beam across a gap 74 between duct 20 and exhaust duct 76. The laser beam is detected by detector 32' which, in turn, transmits an appropriate electronic signal back to source 26 via cable 34. Such an arrangement enables the launcher assembly and detector to be placed away from duct 20 and the high temperature environment of the off-gas. Accuracy concerns are minimized due to the relatively small size of the gap compared to the large diameters of the ducts 20 and 76.

With slightly different laser diodes that still operate in the near-IR, absorption models and limited research indicate the potential to measure $CO_2$, NO, hydrocarbons, HX (where X represents various halogens), and $H_2S$ compounds. By multiplexing additional lasers through a shared optical system (optical launch and receive components, fibre optic transmission cables, laser electronic control components, etc.) the incremental system cost for this measurement capability may be a small fraction of the total system cost since the laser diodes themselves typically represent a small fraction of the total system capital cost. This possibility would extend the benefits of near-IR optical measurement techniques to an extremely wide range of applications.

Moreover, visible lasers offer many of the same advantages of near-IR lasers, including, for example, cost, simple operation, and efficient transmission through conventional fibre optics. Attractive regions for $O_2$ detection lie in the visible wavelengths, especially around 0.76 μm. $NO_2$ detection in the visible wavelengths has been documented around 0.68 μm.

While this technique has been investigated specifically for application in the steel industry, and more specifically for EAFs, there exists tremendous potential for extension to near-IR measurement of additional compounds and application to numerous other combustion devices. Some particular examples can include: steel production (smelting, reheat furnaces, BOFs, etc.); aluminum smelters and other metallurgical applications; potash processing; fossil fuelled power generation plants; incineration; glass furnaces; cement kilns; and recovery boilers in the pulp and paper industry.

It can be appreciated that variations to this invention would be readily apparent to those skilled in the art, and this invention is intended to include those alternatives.

We claim:

1. A method for process control in a steelmaking combustion application, comprising:
    a) transmitting a frequency modulated near-infrared laser beam through off-gas produced by a steelmaking combustion application, the modulation frequency of the laser beam greater than the absorption line width of targeted CO and $H_2O$ produced by the steelmaking combustion application;
    b) detecting the transmitted laser beam;
    c) analyzing the detected laser beam for select CO and $H_2O$ absorption lines;
    d) determining the CO concentration from the CO and $H_2O$ absorption lines; and
    e) adjusting select inputs of the combustion application in response to the CO concentration.

2. A method according to claim 1 wherein CO concentration is determined using predetermined calibration curves.

3. A method according to claim 2 wherein the calibration curve is CO concentration as a function of CO absorption lines and temperature.

4. A method according to claim 3 wherein the $H_2O$ absorption lines are used to determine the temperature of the off-gas.

5. A method according to claim 4 wherein the targeted $H_2O$ has absorption lines that respond differentially to changes in temperature.

6. A method according to claim 4 wherein the temperature of the off-gas is determined from the ratio of two $H_2O$ absorption lines.

7. A method according to claim 1 wherein the targeted CO has a profile of strong absorption lines as compared to $H_2O$.

8. A method according to claim 1 wherein the CO absorption line is located at 1577.96 nm, and the $H_2O$ absorption lines are located at 1577.8 nm and 1578.1 nm.

9. A method according to claim 1 wherein the wavelength of the laser beam is in the range of about 0.7 μm to about 3.0 μm.

10. A method according to claim 1 wherein the near-infrared laser beam is transmitted by a tunable diode laser.

11. A method according to claim 10 wherein the wavelength of the laser beam is in the range of about 1.5 μm to about 1.7 μm.

12. A method according to claim 1 wherein the near-infrared laser beam is transmitted by a distributed feedback laser.

13. A method according to claim 12 wherein the wavelength of the laser beam is in the range of about 1.57 μm to about 1.59 μm.

14. A method according to claim 1 wherein the select inputs to the combustion application comprise oxygen.

15. A method according to claim 1 wherein the select inputs to the combustion application comprise fuel.

16. A method according to claim 1 wherein the select inputs to the combustion application comprise electric power.

17. A method according to claim 14 wherein the select inputs to the combustion application comprise fuel.

18. A method according to claim 14 wherein the select inputs to the combustion application comprise electric power.

19. A method according to claim 15 wherein the select inputs to the combustion application comprise electric power.

20. A method according to claim 17 wherein the select inputs to the combustion application comprise electric power.

21. A method for process control in a steelmaking combustion application, the method comprising:
  a) scanning off-gas produced by a steelmaking combustion application with a laser, the step of scanning comprising:
    i) targeting the off-gas with laser light corresponding to at least one CO absorption, and at least one $H_2O$ absorption, the laser light having a modulation frequency greater than the absorption line width of the targeted CO and $H_2O$ produced by the steelmaking combustion application; and
    ii) refraining from shining laser light on the off-gas during an off-interval,
  b) detecting transmitted laser light of step i),
  c) analyzing the detected laser light for select CO and $H_2O$ absorption lines;
  d) measuring background radiation during the off-interval;
  e) determining the CO concentration from the CO and $H_2O$ absorption lines and from the measured background radiation; and
  f) adjusting select inputs of the combustion application in response to the CO concentration.

22. The method of claim 21, wherein the step of targeting comprises:
  A) transmitting laser light corresponding to CO absorption during a first time interval; and
  B) transmitting laser light corresponding to $H_2O$ absorption during a second time interval that immediately follows the first interval.

23. The method of claim 22, wherein, in the step of determining, the measured background radiation is used to account for at least one of light produced by the combustion application, dust, debris and optical misalignment of the laser.

24. The method of claim 21, wherein steps i) and ii) are repeated periodically.

* * * * *